US011452500B2

(12) United States Patent
Flores, II et al.

(10) Patent No.: US 11,452,500 B2
(45) Date of Patent: Sep. 27, 2022

(54) INTEGRATED PROBE STRUCTURE

(71) Applicant: NovaSignal Corp., Los Angeles, CA (US)

(72) Inventors: Roman Flores, II, Los Angeles, CA (US); Matthew Hutter, Los Angeles, CA (US); Gerard Salinas, Los Angeles, CA (US); Michael Costa, Los Angeles, CA (US); Matthew Sylvester, Los Angeles, CA (US)

(73) Assignee: NovaSignal Corp., Los Angeles, CA (US)

( * ) Notice: Subject to any disclaimer, the term of this patent is extended or adjusted under 35 U.S.C. 154(b) by 234 days.

(21) Appl. No.: 16/847,247

(22) Filed: Apr. 13, 2020

(65) Prior Publication Data

US 2020/0237342 A1 Jul. 30, 2020

Related U.S. Application Data

(63) Continuation of application No. 15/399,440, filed on Jan. 5, 2017, now Pat. No. 10,617,388.

(60) Provisional application No. 62/332,133, filed on May 5, 2016, provisional application No. 62/275,192, filed on Jan. 5, 2016.

(51) Int. Cl.
*A61B 8/00* (2006.01)
*A61B 8/08* (2006.01)

(52) U.S. Cl.
CPC .......... *A61B 8/4444* (2013.01); *A61B 8/0808* (2013.01); *A61B 8/4209* (2013.01); *A61B 8/488* (2013.01)

(58) Field of Classification Search
CPC ... A61B 8/4444; A61B 8/4209; A61B 8/0808; A61B 8/488
See application file for complete search history.

(56) References Cited

U.S. PATENT DOCUMENTS

| | | |
|---|---|---|
| 3,841,308 A | 10/1974 | Tate |
| 3,872,858 A | 3/1975 | Hudson et al. |
| 4,204,547 A | 5/1980 | Allocca |
| 4,205,687 A | 6/1980 | White et al. |
| 4,413,629 A | 11/1983 | Durley, III |
| 4,483,344 A | 11/1984 | Atkov et al. |
| 4,559,952 A | 12/1985 | Angelsen et al. |
| 4,759,374 A | 7/1988 | Kierney et al. |
| 4,815,705 A | 3/1989 | Kasugai et al. |
| 4,819,648 A | 4/1989 | Ko |

(Continued)

FOREIGN PATENT DOCUMENTS

| | | |
|---|---|---|
| CN | 104605889 A | 5/2015 |
| EP | 0 403 807 A2 | 12/1990 |

(Continued)

OTHER PUBLICATIONS

Japanese Office Action dated Mar. 11, 2021, from application No. 2018-555541.

(Continued)

*Primary Examiner* — Rex R Holmes
(74) *Attorney, Agent, or Firm* — Foley & Lardner LLP

(57) ABSTRACT

According to various embodiments, there is provided a probe structure. The probe structure includes a probe configured to emit acoustic energy. The probe structure further includes a load cell underneath and aligned with the probe. The probe structure further includes a probe hub including a cavity for receiving the probe and the load cell.

20 Claims, 16 Drawing Sheets

(56) References Cited

U.S. PATENT DOCUMENTS

| | | |
|---|---|---|
| 4,841,986 A | 6/1989 | Marchbanks |
| 4,930,513 A | 6/1990 | Mayo et al. |
| 4,951,653 A | 8/1990 | Fry et al. |
| 4,984,567 A | 1/1991 | Kageyama et al. |
| 5,040,540 A | 8/1991 | Sackner |
| 5,074,310 A | 12/1991 | Mick |
| 5,094,243 A | 3/1992 | Puy et al. |
| 5,156,152 A | 10/1992 | Yamazaki et al. |
| 5,197,019 A | 3/1993 | Delon-Martin et al. |
| 5,348,015 A | 9/1994 | Moehring et al. |
| 5,379,770 A | 1/1995 | Van Veen |
| 5,388,583 A | 2/1995 | Ragauskas et al. |
| 5,409,005 A | 4/1995 | Bissonnette et al. |
| 5,409,010 A | 4/1995 | Beach et al. |
| 5,411,028 A | 5/1995 | Bonnefous |
| 5,421,565 A | 6/1995 | Harkrader et al. |
| 5,514,146 A | 5/1996 | Lam et al. |
| 5,522,392 A | 6/1996 | Suorsa et al. |
| 5,526,299 A | 6/1996 | Coifman et al. |
| 5,617,873 A | 4/1997 | Yost et al. |
| 5,840,018 A | 11/1998 | Michaeli |
| 5,860,929 A | 1/1999 | Rubin et al. |
| 5,871,445 A | 2/1999 | Bucholz |
| 5,899,864 A | 5/1999 | Arenson et al. |
| 5,919,144 A | 7/1999 | Bridger et al. |
| 5,951,477 A | 9/1999 | Ragauskas et al. |
| 5,993,398 A | 11/1999 | Alperin |
| 6,027,454 A | 2/2000 | Low |
| 6,117,089 A | 9/2000 | Sinha |
| 6,120,446 A | 9/2000 | Ji et al. |
| 6,129,682 A | 10/2000 | Borchert et al. |
| 6,135,957 A | 10/2000 | Cohen-Bacrie et al. |
| 6,139,499 A | 10/2000 | Wilk |
| 6,200,267 B1 | 3/2001 | Burke |
| 6,231,509 B1 | 5/2001 | Johnson et al. |
| 6,261,231 B1 | 7/2001 | Damphousse et al. |
| 6,309,354 B1 | 10/2001 | Madsen et al. |
| 6,358,239 B1 | 3/2002 | Rake et al. |
| 6,364,869 B1 | 4/2002 | Bonaldo |
| 6,387,051 B1 | 5/2002 | Ragauskas et al. |
| 6,403,056 B1 | 6/2002 | Unger |
| 6,413,227 B1 | 7/2002 | Yost et al. |
| 6,423,003 B1 | 7/2002 | Ustuner et al. |
| 6,425,865 B1 | 7/2002 | Salcudean et al. |
| 6,454,715 B2 | 9/2002 | Teo |
| 6,488,717 B1 | 12/2002 | McColl et al. |
| 6,491,647 B1 | 12/2002 | Bridger et al. |
| 6,503,202 B1 | 1/2003 | Hossack et al. |
| 6,547,731 B1 | 4/2003 | Coleman et al. |
| 6,547,734 B2 | 4/2003 | Madsen et al. |
| 6,547,737 B2 | 4/2003 | Njemanze |
| 6,589,189 B2 | 7/2003 | Meyerson et al. |
| 6,618,493 B1 | 9/2003 | Torp et al. |
| 6,627,421 B1 | 9/2003 | Unger et al. |
| 6,653,825 B2 | 11/2003 | Munniksma |
| 6,656,125 B2 | 12/2003 | Misczynski et al. |
| 6,682,488 B2 | 1/2004 | Abend |
| 6,702,743 B2 | 3/2004 | Michaeli |
| 6,716,412 B2 | 4/2004 | Unger |
| 6,740,048 B2 | 5/2004 | Yost et al. |
| 6,746,422 B1 | 6/2004 | Noriega et al. |
| 6,875,176 B2 | 4/2005 | Mourad et al. |
| 6,887,199 B2 | 5/2005 | Bridger et al. |
| 6,955,648 B2 | 10/2005 | Mozayeni et al. |
| 7,122,007 B2 | 10/2006 | Querfurth |
| 7,128,713 B2 | 10/2006 | Moehring et al. |
| 7,147,605 B2 | 12/2006 | Ragauskas |
| 7,302,064 B2 | 11/2007 | Causevic et al. |
| 7,338,450 B2 | 3/2008 | Kristoffersen et al. |
| 7,403,805 B2 | 7/2008 | Abreu |
| 7,452,551 B1 | 11/2008 | Unger et al. |
| 7,534,209 B2 | 5/2009 | Abend et al. |
| 7,537,568 B2 | 5/2009 | Moehring |
| D594,127 S | 6/2009 | Causevic et al. |
| 7,547,283 B2 | 6/2009 | Mourad et al. |
| D603,051 S | 10/2009 | Causevic et al. |
| 7,674,229 B2 | 3/2010 | Hynynen et al. |
| 7,720,530 B2 | 5/2010 | Causevic |
| 7,771,358 B2 | 8/2010 | Moehring et al. |
| 7,815,574 B2 | 10/2010 | Mourad et al. |
| 7,854,701 B2 | 12/2010 | Stergiopoulos et al. |
| 7,857,763 B2 | 12/2010 | Tai |
| 7,904,144 B2 | 3/2011 | Causevic et al. |
| 7,912,269 B2 | 3/2011 | Ikeda et al. |
| 7,938,780 B2 | 5/2011 | Ragauskas et al. |
| 7,942,820 B2 | 5/2011 | Njemanze |
| D641,886 S | 7/2011 | Causevic et al. |
| 7,998,075 B2 | 8/2011 | Ragauskas et al. |
| RE42,803 E | 10/2011 | Lipson et al. |
| 8,036,856 B2 | 10/2011 | Pan et al. |
| 8,041,136 B2 | 10/2011 | Causevic |
| 8,062,224 B2 | 11/2011 | Ragauskas et al. |
| 8,075,488 B2 | 12/2011 | Burton |
| 8,109,880 B1 | 2/2012 | Pranevicius et al. |
| 8,162,837 B2 | 4/2012 | Moehring et al. |
| 8,206,303 B2 | 6/2012 | Ragauskas et al. |
| 8,211,023 B2 | 7/2012 | Swan et al. |
| 8,235,907 B2 | 8/2012 | Wilk et al. |
| 8,254,654 B2 | 8/2012 | Yen et al. |
| 8,265,291 B2 | 9/2012 | Bridger et al. |
| 8,353,853 B1 | 1/2013 | Kyle et al. |
| 8,364,254 B2 | 1/2013 | Jacquin et al. |
| 8,364,255 B2 | 1/2013 | Isenhart et al. |
| 8,366,627 B2 | 2/2013 | Kashif et al. |
| 8,391,948 B2 | 3/2013 | Causevic et al. |
| 8,394,024 B2 | 3/2013 | Miyama et al. |
| 8,394,025 B2 | 3/2013 | Ragauskas et al. |
| 8,414,539 B1 | 4/2013 | Kuracina et al. |
| 8,453,509 B2 | 6/2013 | Oberdorfer et al. |
| 8,473,024 B2 | 6/2013 | Causevic et al. |
| 8,603,014 B2 | 12/2013 | Alleman et al. |
| 8,613,714 B2 | 12/2013 | Alleman et al. |
| 8,622,912 B2 | 1/2014 | Chin et al. |
| 8,647,278 B2 | 2/2014 | Ji et al. |
| 8,706,205 B2 | 4/2014 | Shahaf et al. |
| 8,834,376 B2 | 9/2014 | Stergiopoulos et al. |
| 8,905,932 B2 | 12/2014 | Lovoi et al. |
| 8,926,515 B2 | 1/2015 | Ragauskas et al. |
| 8,998,818 B2 | 4/2015 | Pranevicius et al. |
| 9,005,126 B2 | 4/2015 | Beach et al. |
| 9,028,416 B2 | 5/2015 | De Viterbo |
| 9,042,201 B2 | 5/2015 | Tyler et al. |
| 9,066,679 B2 | 6/2015 | Beach et al. |
| 9,125,616 B2 | 9/2015 | Bredno et al. |
| 9,138,154 B2 | 9/2015 | Weinberg et al. |
| 9,192,359 B2 | 11/2015 | Flynn et al. |
| 9,196,037 B2 | 11/2015 | Jung |
| 9,630,028 B2 | 4/2017 | Browning et al. |
| RE46,614 E | 11/2017 | Lipson et al. |
| 10,709,417 B2 | 7/2020 | O'Brien et al. |
| 2001/0053879 A1 | 12/2001 | Mills et al. |
| 2002/0103436 A1 | 8/2002 | Njemanze |
| 2003/0050607 A1 | 3/2003 | Gagnieux et al. |
| 2004/0267127 A1 | 12/2004 | Abend et al. |
| 2005/0004457 A1 | 1/2005 | Moilanen et al. |
| 2005/0004468 A1 | 1/2005 | Abend et al. |
| 2005/0015009 A1 | 1/2005 | Mourad et al. |
| 2005/0049515 A1 | 3/2005 | Misczynski et al. |
| 2005/0119573 A1 | 6/2005 | Vilenkin et al. |
| 2005/0124901 A1 | 6/2005 | Misczynski et al. |
| 2005/0147297 A1 | 7/2005 | McLaughlin et al. |
| 2005/0148895 A1 | 7/2005 | Misczynski et al. |
| 2006/0025801 A1 | 2/2006 | Lulo et al. |
| 2006/0030777 A1 | 2/2006 | Liang et al. |
| 2006/0049721 A1 | 3/2006 | Kuehnicke |
| 2006/0173307 A1 | 8/2006 | Amara et al. |
| 2006/0173337 A1 | 8/2006 | Chen et al. |
| 2006/0184070 A1 | 8/2006 | Hansmann et al. |
| 2006/0206037 A1 | 9/2006 | Braxton |
| 2006/0241462 A1 | 10/2006 | Chou et al. |
| 2007/0016046 A1 | 1/2007 | Mozayeni et al. |
| 2007/0016050 A1 | 1/2007 | Moehring et al. |
| 2007/0078345 A1 | 4/2007 | Mo et al. |
| 2007/0161891 A1 | 7/2007 | Moore et al. |

(56) References Cited

U.S. PATENT DOCUMENTS

| | | |
|---|---|---|
| 2007/0232918 A1 | 10/2007 | Taylor |
| 2007/0239019 A1 | 10/2007 | Richard et al. |
| 2007/0244398 A1 | 10/2007 | Lo et al. |
| 2008/0015478 A1 | 1/2008 | Bose |
| 2008/0058861 A1 | 3/2008 | Cooper et al. |
| 2008/0065099 A1 | 3/2008 | Cooper et al. |
| 2008/0132790 A1 | 6/2008 | Burton |
| 2008/0208060 A1 | 8/2008 | Murkin |
| 2008/0262350 A1 | 10/2008 | Unger |
| 2009/0062813 A1 | 3/2009 | Prisco et al. |
| 2009/0074151 A1 | 3/2009 | Henderson et al. |
| 2009/0198137 A1 | 8/2009 | Ragauskas et al. |
| 2009/0264786 A1 | 10/2009 | Jacquin |
| 2009/0275836 A1 | 11/2009 | Fujii et al. |
| 2009/0287084 A1 | 11/2009 | Ragauskas et al. |
| 2009/0306515 A1 | 12/2009 | Matsumura et al. |
| 2009/0326379 A1 | 12/2009 | Daigle et al. |
| 2010/0016707 A1 | 1/2010 | Amara et al. |
| 2010/0069757 A1 | 3/2010 | Yoshikawa et al. |
| 2010/0081893 A1 | 4/2010 | Jarvik et al. |
| 2010/0087728 A1 | 4/2010 | Jarvik et al. |
| 2010/0121192 A1 | 5/2010 | Nogata et al. |
| 2010/0125206 A1 | 5/2010 | Syme |
| 2010/0130866 A1 | 5/2010 | Main et al. |
| 2010/0274303 A1 | 10/2010 | Bukhman |
| 2010/0298821 A1 | 11/2010 | Garbagnati |
| 2011/0112426 A1 | 5/2011 | Causevic |
| 2011/0137182 A1 | 6/2011 | Bellezza et al. |
| 2011/0144518 A1 | 6/2011 | Causevic |
| 2011/0251489 A1 | 10/2011 | Zhang et al. |
| 2011/0275936 A1 | 11/2011 | Cho et al. |
| 2011/0301461 A1 | 12/2011 | Anite |
| 2012/0108967 A1 | 5/2012 | Weng et al. |
| 2012/0108972 A1 | 5/2012 | Miyama et al. |
| 2012/0123272 A1 | 5/2012 | Lam et al. |
| 2012/0123590 A1 | 5/2012 | Halsmer |
| 2012/0153580 A1 | 6/2012 | Soma |
| 2012/0157840 A1 | 6/2012 | Syme |
| 2012/0165675 A1 | 6/2012 | Syme |
| 2012/0165676 A1 | 6/2012 | Njemanze |
| 2012/0226163 A1 | 9/2012 | Moehring et al. |
| 2012/0238875 A1 | 9/2012 | Savitsky et al. |
| 2013/0006106 A1 | 1/2013 | O'Reilly et al. |
| 2013/0018277 A1 | 1/2013 | Liu |
| 2013/0047452 A1 | 2/2013 | McMurtry et al. |
| 2013/0080127 A1 | 3/2013 | Shahaf et al. |
| 2013/0197401 A1 | 8/2013 | Sato et al. |
| 2013/0239687 A1 | 9/2013 | Nakabayashi |
| 2013/0274607 A1 | 10/2013 | Anand et al. |
| 2014/0031690 A1 | 1/2014 | Toji et al. |
| 2014/0031693 A1 | 1/2014 | Solek |
| 2014/0081142 A1 | 3/2014 | Toma et al. |
| 2014/0081144 A1 | 3/2014 | Moehring et al. |
| 2014/0094701 A1 | 4/2014 | Kwartowitz et al. |
| 2014/0163328 A1 | 6/2014 | Geva et al. |
| 2014/0163379 A1 | 6/2014 | Bukhman |
| 2014/0171820 A1 | 6/2014 | Causevic |
| 2014/0194740 A1 | 7/2014 | Stein et al. |
| 2014/0276059 A1 | 9/2014 | Sheehan |
| 2014/0316269 A1 | 10/2014 | Zhang et al. |
| 2014/0323857 A1 | 10/2014 | Mourad et al. |
| 2014/0343431 A1 | 11/2014 | Vajinepalli et al. |
| 2015/0051489 A1 | 2/2015 | Caluser et al. |
| 2015/0065871 A1 | 3/2015 | Konofagou et al. |
| 2015/0065916 A1 | 3/2015 | Maguire et al. |
| 2015/0094582 A1 | 4/2015 | Tanaka et al. |
| 2015/0151142 A1 | 6/2015 | Tyler et al. |
| 2015/0157266 A1 | 6/2015 | Machon et al. |
| 2015/0190111 A1 | 7/2015 | Fry |
| 2015/0216500 A1 | 8/2015 | Mano et al. |
| 2015/0245771 A1 | 9/2015 | Wang et al. |
| 2015/0245776 A1 | 9/2015 | Hirohata et al. |
| 2015/0245820 A1 | 9/2015 | Tamada |
| 2015/0250446 A1 | 9/2015 | Kanayama |
| 2015/0250448 A1 | 9/2015 | Tamada |
| 2015/0297176 A1 | 10/2015 | Rincker et al. |
| 2015/0297177 A1 | 10/2015 | Boctor et al. |
| 2015/0302584 A1 | 10/2015 | Brauner et al. |
| 2015/0351718 A1 | 12/2015 | Vollmer et al. |
| 2015/0356734 A1 | 12/2015 | Ooga et al. |
| 2015/0359448 A1 | 12/2015 | Beach |
| 2016/0000367 A1 | 1/2016 | Lyon |
| 2016/0000411 A1 | 1/2016 | Raju et al. |
| 2016/0000516 A1 | 1/2016 | Cheng et al. |
| 2016/0030001 A1 | 2/2016 | Stein et al. |
| 2016/0094115 A1 | 3/2016 | Okawa et al. |
| 2016/0151618 A1 | 6/2016 | Powers et al. |
| 2016/0256130 A1 | 9/2016 | Hamilton et al. |
| 2016/0278736 A1 | 9/2016 | Hamilton et al. |
| 2016/0310006 A1 | 10/2016 | Aguero Villarreal et al. |
| 2016/0310023 A1 | 10/2016 | Chachisvilis et al. |
| 2016/0317129 A1 | 11/2016 | Seip et al. |
| 2016/0324585 A1 | 11/2016 | Noonan et al. |
| 2016/0367217 A1 | 12/2016 | Flores et al. |
| 2017/0119347 A1 | 5/2017 | Flores et al. |
| 2017/0188992 A1 | 7/2017 | O'Brien et al. |
| 2017/0188993 A1 | 7/2017 | Hamilton et al. |
| 2017/0188994 A1 | 7/2017 | Flores et al. |
| 2017/0196465 A1 | 7/2017 | Browning et al. |
| 2017/0307420 A1 | 10/2017 | Flores et al. |
| 2018/0021021 A1 | 1/2018 | Zwierstra et al. |
| 2018/0093077 A1 | 4/2018 | Harding et al. |
| 2018/0103927 A1 | 4/2018 | Chung et al. |
| 2018/0103928 A1 | 4/2018 | Costa et al. |
| 2018/0177487 A1 | 6/2018 | Deffieux et al. |
| 2018/0214124 A1 | 8/2018 | O'Brien et al. |
| 2018/0220991 A1 | 8/2018 | O'Brien et al. |
| 2019/0150895 A1 | 5/2019 | Tian et al. |

FOREIGN PATENT DOCUMENTS

| | | |
|---|---|---|
| EP | 1 750 804 | 2/2007 |
| EP | 2 034 901 A1 | 3/2009 |
| EP | 2 111 787 A1 | 10/2009 |
| EP | 2 858 619 A1 | 4/2015 |
| FR | 2606625 A1 | 5/1988 |
| JP | S52-126979 A | 10/1977 |
| JP | H02-114008 | 4/1990 |
| JP | H05-143161 | 6/1993 |
| JP | H571763 U | 9/1993 |
| JP | 07-299066 A | 11/1995 |
| JP | H07-299066 A | 11/1995 |
| JP | 10-328189 A | 12/1998 |
| JP | H10-328189 A | 12/1998 |
| JP | 2003-225239 A | 8/2003 |
| JP | 2003-230558 A | 8/2003 |
| JP | 2003-245280 A | 9/2003 |
| JP | 2004-237082 A | 8/2004 |
| JP | 2006-025904 A | 2/2006 |
| JP | 2007-143704 A | 6/2007 |
| JP | 2010-500084 A | 1/2010 |
| JP | 2010-200844 A | 9/2010 |
| JP | 2013-503681 A | 2/2013 |
| JP | 2015-533299 A | 11/2015 |
| WO | WO-95/02361 A1 | 1/1995 |
| WO | WO-99/56625 A1 | 11/1999 |
| WO | WO-2009/138882 A2 | 11/2009 |
| WO | WO-2010/042146 A2 | 4/2010 |
| WO | WO-2013/155537 A1 | 10/2013 |
| WO | WO-2014/070993 A1 | 5/2014 |
| WO | WO-2015/073903 A1 | 5/2015 |
| WO | WO-2015/092604 A1 | 6/2015 |
| WO | WO-2016/001548 A1 | 1/2016 |

OTHER PUBLICATIONS

Notice of Allowance dated Mar. 19, 2021, from U.S. Appl. No. 15/399,710.

Aaslid, R., et al., "Noninvasive transcranial Doppler ultrasound recording of flow velocity in basal cerebral arteries", Journal of Neurosurgery, 1982, 57(6): p. 769-774.

Baldwin, K., et al., "Subpeak Regional Analysis of Intracranial Pressure Waveform Morphology based on Cerebrospinal Fluid

(56) References Cited

OTHER PUBLICATIONS

Hydrodynamics in the Cerebral Aqueduct and Prepontine Cistern", 34th Annual International Conference of the IEEE EMBS, 2012, p. 3935-3938.

Bashford, G., et al.,"Monitoring Cerebral Hemodynamics with Transcranial Doppler Ultrasound during Cognitive and Exercise Testing in Adults following Unilateral Stroke", 34th Annual International Conference of the IEEE EMBS, 2012, p. 2310-2313.

Chatelain et al. "Confidence-Driven Control of an Ultrasound Probe: Target-Specific Acoustic Window Optimization." IEEE ICRA May 16-21, 2016, pp. 3441-3446.

Chatelain et al. "Optimization of ultrasound image quality via visual servoing." IEEE INCRA May 26-30, 2015, pp. 5997-6002.

Chen, W., et al., "Intracranial Pressure Level Prediction in Traumatic Brain Injury by Extracting Features from Multiple Sources and Using Machine Learning Methods", 2010 IEEE International Conference on Bioinformatics and Biomedicine, 2010, p. 510-515.

Cheng, Y. & Zhao, R., "Self-training classifier via local learning regularization", Proceedings of the Eighth International Conference on Machine Learning and Cybernetics, 2009, p. 454-459.

Ekroth, R., et al., "Transcranial Doppler-estimated versus thermodilution estimated cerebral blood flow during cardiac operations. Influence of temperature and arterial carbon dioxide tension." Journal Thoracic Cardiovascular Surgery, 1991, 102(1): p. 95-102.

Extended European Search Report dated Jan. 4, 2019, from application No. 16812644.9.

Extended European Search Report dated Jul. 16, 2019, from application No. 17736353.8.

Extended European Search Report dated Jul. 19, 2019, from application No. 17736375.1.

Extended European Search Report dated Jul. 24, 2019, from application No. 17735919.7.

Extended European Search Report dated Nov. 12, 2019, from application No. 17736371.0.

Extended European Search Report dated Nov. 21, 2019, from application No. 17790294.7.

Final Office Action dated Aug. 2, 2019, from U.S. Appl. No. 15/399,648.

Final Office Action dated Aug. 28, 2019, from U.S. Appl. No. 15/399,440.

Final Office Action dated Jan. 28, 2019, from U.S. Appl. No. 15/942,368.

Final Office Action dated Jan. 30, 2020, from U.S. Appl. No. 15/497,039.

Gomez, C., et al., Transcranial Doppler Ultrasonographic Assessment of Intermittent Light Stimulation at Different Frequencies, Stroke, 1990, 21, p. 1746-1748.

Harrison, M. & Markus, H., "Estimation of cerebrovascular reactivity using transcranial Doppler, including the use of breath-holding as the vasodilatory stimulus", Stroke, 1992, 23(5) p. 668-673.

International Preliminary Report on Patentability dated Dec. 28, 2017, from international application No. PCT/US2016/038433.

International Preliminary Report on Patentability dated Jul. 19, 2018, from application No. PCT/IB2017/050349.

International Preliminary Report on Patentability dated Jul. 19, 2018, from application No. PCT/US2017/012365.

International Preliminary Report on Patentability dated Jul. 19, 2018, from application No. PCT/US2017/012395.

International Preliminary Report on Patentability dated Jul. 19, 2018, from application No. PCT/US2017/012402.

International Preliminary Report on Patentability dated Nov. 8, 2018, from application No. PCT/US2017/029483.

International Search Report and Written Opinion dated Aug. 14, 2017, from international application No. PCT/US2017/029483.

International Search Report and Written Opinion dated May 4, 2017, from application No. PCT/US2017/012395.

International Search Report and Written Opinion dated Oct. 13, 2016, from related international application No. PCT/US2016/038433.

International Search Report and Written Opinion dated Jun. 1, 2017, from application No. PCT/IB2017/050349.

International Search Report and Written Opinion dated Jun. 8, 2017, from application No. PCT/US2017/012402.

Jaffres, P., et al., "Transcranial Doppler to detection admission patients at risk for neurological deterioration following mild and moderate brain trauma", Intensive Care Med, 2005, 31 (6): p. 785-790.

Japanese Decision of Rejection dated Dec. 18, 2018, from application No. 2016-554529.

Japanese Office Action dated Apr. 24, 2018, from application No. 2016-554529.

Japanese Office Action dated Aug. 28, 2018, from application No. 2016-554529.

Japanese Office Action dated Jan. 27, 2020, from application No. 2018-534127.

Len, T.K., et al., "Cerebrovascular reactivity impairment after sport-induced concussion", Med Sci Sports Exerc, 2011, 43(12): p. 2241-2248.

M.H. Raibert et al., "Hybrid Position/Force Control of Manipulators", Journal of Dynamic Systems, Measurement, and Control, vol. 102, Jun. 1981, pp. 126-133, abstract.

Mackinnon et al. "Long-Term Ambulatory Monitoring for Cerebral Emboli Using Transcranial Doppler Ultrasound." Stroke(35), 2004; pp. 73-78.

Nadeau et al. "Intensity-Based Ultrasound Visual Servoing: Modeling and Validation with 2-D and 3-D Probes." IEEE Trans on Robotics (29:4), Aug. 2013, pp. 1003-1015.

Ni, et al., "Serial Transcranial Doppler Sonography in Ischemic Strokes in Middle Cerebral Artery Territory", Journal of Neruoimaging, Oct. 1, 1994, pp. 232-236.

Non-Final Office Action dated Apr. 2, 2019, from U.S. Appl. No. 15/399,440.

Non-Final Office Action dated Aug. 14, 2019, from U.S. Appl. No. 15/497,039.

Non-Final Office Action dated Dec. 11, 2019, from U.S. Appl. No. 15/399,710.

Non-Final Office Action dated Jun. 27, 2018, from U.S. Appl. No. 15/942,368.

Non-Final Office Action dated Jun. 28, 2018, from U.S. Appl. No. 15/940,925.

Non-Final Office Action dated Mar. 19, 2019, from U.S. Appl. No. 15/399,648.

Non-Final Office Action dated Nov. 19, 2019, from U.S. Appl. No. 15/399,648.

Non-Final Office Action dated Oct. 1, 2019, from U.S. Appl. No. 15/399,735.

Non-Final Office Action dated Sep. 17, 2018, from U.S. Appl. No. 15/156,175.

Notice of Allowance dated Dec. 9, 2019, from U.S. Appl. No. 15/399,440.

Notice of Allowance dated Mar. 4, 2020, from U.S. Appl. No. 15/942,368.

Qiu, et al., "A Robotic Holder of Transcranial Doppler Probe for CBFV Auto-Searching", 2013 IEEE International Conference on Information and Automation (ICIA), IEEE, Aug. 26, 2013, pp. 1284-1289.

Souza-Daw et al. "Towards Ultrasonic Detection of Acoustic Windows for Transcranial Doppler Ultrasound and related Procedures." IEEE Proc INDS'11 & ISTET'11. Jul. 25-27, 2011. 6 pages.

Tatasurya, Samuel Radiant, "Multimodal Graphical User Interface for Ultrasound Machine Control via da Vinci Surgeon Console: Design, Development, and Initial Evaluation," The University of British Columbia, Vancouver, Aug. 2015, p. 33, paragraph 1.

Uguz, H., "A hybrid system based on information gain and principal component analysis for the classification of transcranial Doppler signals", Computer Methods and Programs in Biomedicine, 2010, 107(2012) p. 598-609.

Zhu, X., "Semi-supervised Learning Literature Survey", Computer Sciences TR 1530, University of Wisconsin-Madison, 2008.

Japanese Office Action dated Dec. 10, 2020, from application No. 2018-534916.

(56) References Cited

OTHER PUBLICATIONS

Non-Final Office Action dated Dec. 8, 2021, from U.S. Appl. No. 15/399,735.
Chinese Office Action dated Aug. 27, 2020, from application No. 201780005528.X.
Chinese Office Action dated Sep. 23, 2020, from application No. 201780005865.9.
Japanese Office Action dated Nov. 5, 2020, from application No. 2018-534904.
Japanese Office Action dated Oct. 22, 2020, from application No. 2018-534131.
Non-Final Office Action dated Oct. 28, 2020, from U.S. Appl. No. 15/187,397.
Final Office Action dated Jun. 15, 2020, from U.S. Appl. No. 15/399,735.
Final Office Action dated Jun. 9, 2020, from U.S. Appl. No. 15/399,648.
Non-Final Office Action dated Jul. 16, 2020, from U.S. Appl. No. 15/497,039.
Final Office Action dated Apr. 23, 2021, from U.S. Appl. No. 15/187,397.
Chinese Office Action dated Mar. 24, 2020, from application No. 201680034144.6.
Chinese Office Action dated Aug. 18, 2020, from application No. 201780005508.2.
Chinese Office Action dated Jun. 30, 2020, from application No. 201780005447.X.
Final Office Action dated Sep. 18, 2020, from U.S. Appl. No. 15/399,710.
European Office Action dated Sep. 24, 2021, from application No. 17735919.7.
European Office Action dated Sep. 28, 2021, from application No. 17736375.1.
Notice of Allowance dated Aug. 24, 2021, from U.S. Appl. No. 15/187,397.

1200

INTEGRATED PROBE STRUCTURE

CROSS-REFERENCE TO RELATED APPLICATIONS

This application is a continuation of U.S. application Ser. No. 15/399,440, filed Jan. 5, 2017, now U.S. Pat. No. 10,617,388, granted Apr. 14, 2020, which claims the benefit of and priority to U.S. Provisional Application No. 62/332,133, filed May 5, 2016, and U.S. Provisional Application No. 62/275,192, filed Jan. 5, 2016, the contents of which are incorporated herein by reference in their entireties.

BACKGROUND

1. Field

Subject matter described herein relates generally to medical devices, and more particularly to a probe for diagnosing medical conditions.

2. Background

For devices utilizing a probe (e.g., an automated Transcranial Doppler (TCD) device), there exist patient safety concerns related to the placement and alignment of TCD probes against a human being's skull. This safety concern exists within the structure of an automated robotic headset or manual operation of TCD probes. In existing solutions, either manual placement of the TCD probe or the complexity of the TCD probe mechanism may not be optimal. Currently there is no method to observe the amount of pressure or force exerted on a patient's temporal window or skull and thus there are no mediums to monitor patient discomfort during an automated or manual TCD probe placement.

SUMMARY

In general, various embodiments relate to systems and methods for providing an integrated probe structure incorporating a probe integrated with a gimbal structure or probe hub.

According to various embodiments, there is provided a probe structure. The probe structure includes a probe configured to emit acoustic energy. The probe structure further includes a load cell underneath and aligned with the probe. The probe structure further includes a probe hub including a cavity for receiving the probe and the load cell.

In some embodiments, the probe structure further includes a probe seat interposed between the probe and the load cell.

In some embodiments, the probe hub includes a lengthwise slot.

In some embodiments, the lengthwise slot is configured to align and retain a cable connected to the probe and a wire connected to the load cell.

In some embodiments, the wire connected to the load cell is held statically within the lengthwise slot while the cable of the probe is configured to move along the lengthwise slot.

In some embodiments, the probe structure further includes an adhesive layer between the load cell and a bottom of the cavity of the probe hub.

In some embodiments, the load cell further includes a probe seat interposed between the probe and the load cell and an adhesive layer between the probe and the probe seat.

In some embodiments, the adhesive layer includes epoxy.

In some embodiments, the load cell includes a protrusion and the probe includes a hollow for receiving the protrusion for securing the load cell and the probe together.

In some embodiments, the probe structure further includes a probe seat interposed between the probe and the load cell, wherein the probe seat has a through hole such that the protrusion of the load cell threads through the through hole and the hollow of the probe.

In some embodiments, the probe hub is configured to house the load cell and a portion of the probe.

In some embodiments, the cavity of the probe hub includes an inner diameter that is substantially equal to an outer diameter of the portion of the probe.

In some embodiments, the cavity of the probe hub includes a first inner diameter corresponding to a location of the portion of the probe housed within the cavity and a second inner diameter corresponding to a location of the load cell housed within the cavity, the first inner diameter being different from the second inner diameter.

In some embodiments, the first inner diameter is greater than the second inner diameter.

In some embodiments, the first inner diameter is substantially equal to an outer diameter of the portion of the probe and the second inner diameter is substantially equal to an outer diameter of the load cell.

In some embodiments, the probe structure further includes a probe seat interposed between the probe and the load cell, wherein the first inner diameter further corresponds to a location of the probe seat housed within the cavity.

In some embodiments, the load cell is configured to detect forces exerted against the probe along a plurality of axes.

In some embodiments, the probe includes a transcranial Doppler (TCD) probe.

According to various embodiments, there is provided a method of manufacturing a probe structure. The method includes providing a probe configured to emit acoustic energy. The method further includes aligning a load cell underneath the probe. The method further includes providing a probe hub including a cavity for receiving the probe and the load cell.

According to various embodiments, there is provided a system for detecting neurological conditions of a subject. The system includes automated robotics configured to position a probe structure with respect to the subject. The probe structure includes a probe configured to emit acoustic energy. The probe structure further includes a load cell underneath and aligned with the probe. The probe structure further includes a probe hub including a cavity for receiving the probe and the load cell.

DETAILED DESCRIPTION

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

Figure 1:
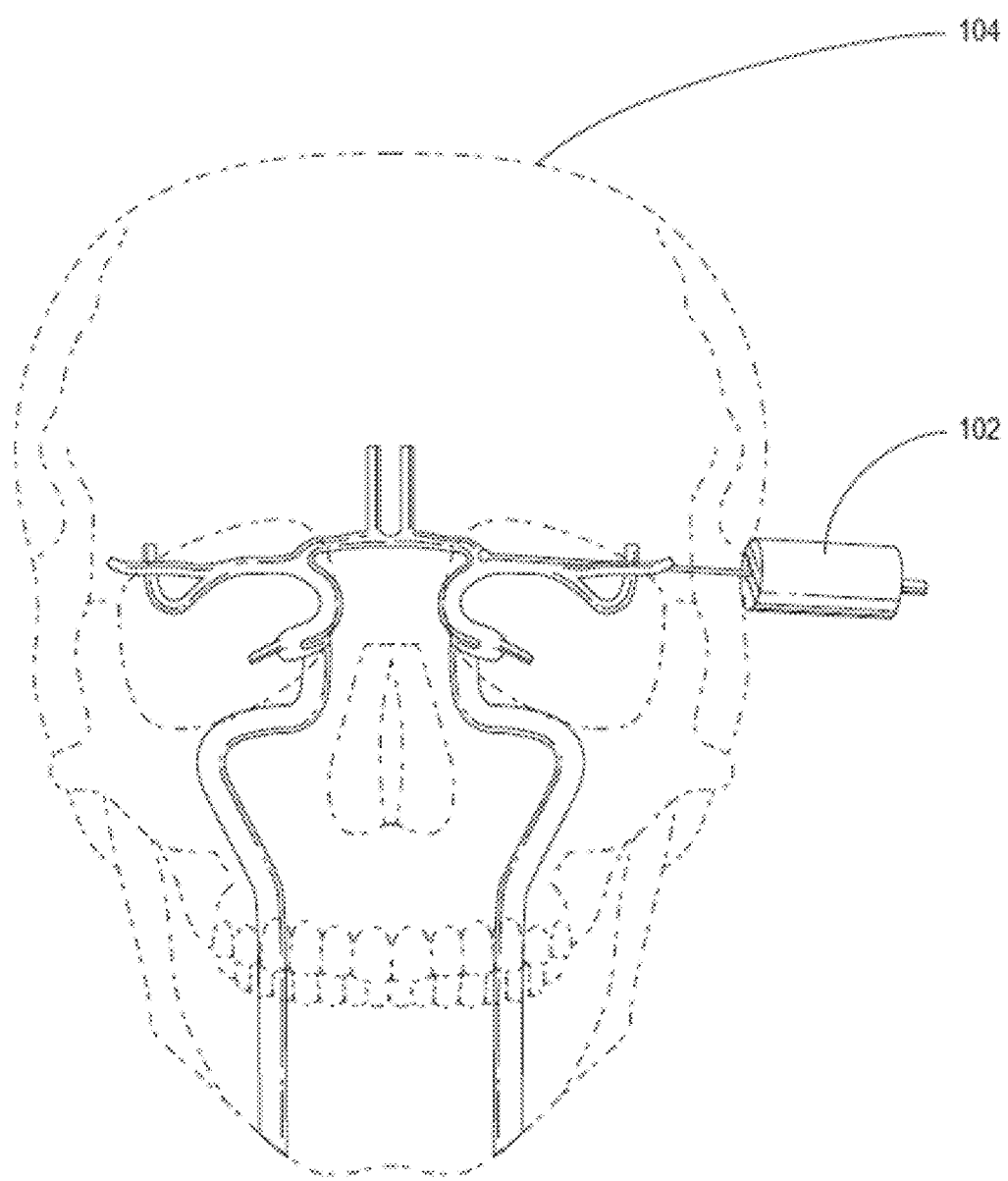
FIG. 1 illustrates a perspective view of a TCD probe previously known in the art.

FIG. 1 illustrates a side view of a prior art TCD probe 102 pressed against a human being's skull 104. In the prior art, when a TCD probe 102 was manipulated by a human operator (e.g., a skilled sonographer operating a TCD probe), it was not critical to reduce the size of the TCD probe 102.

Figure 2:
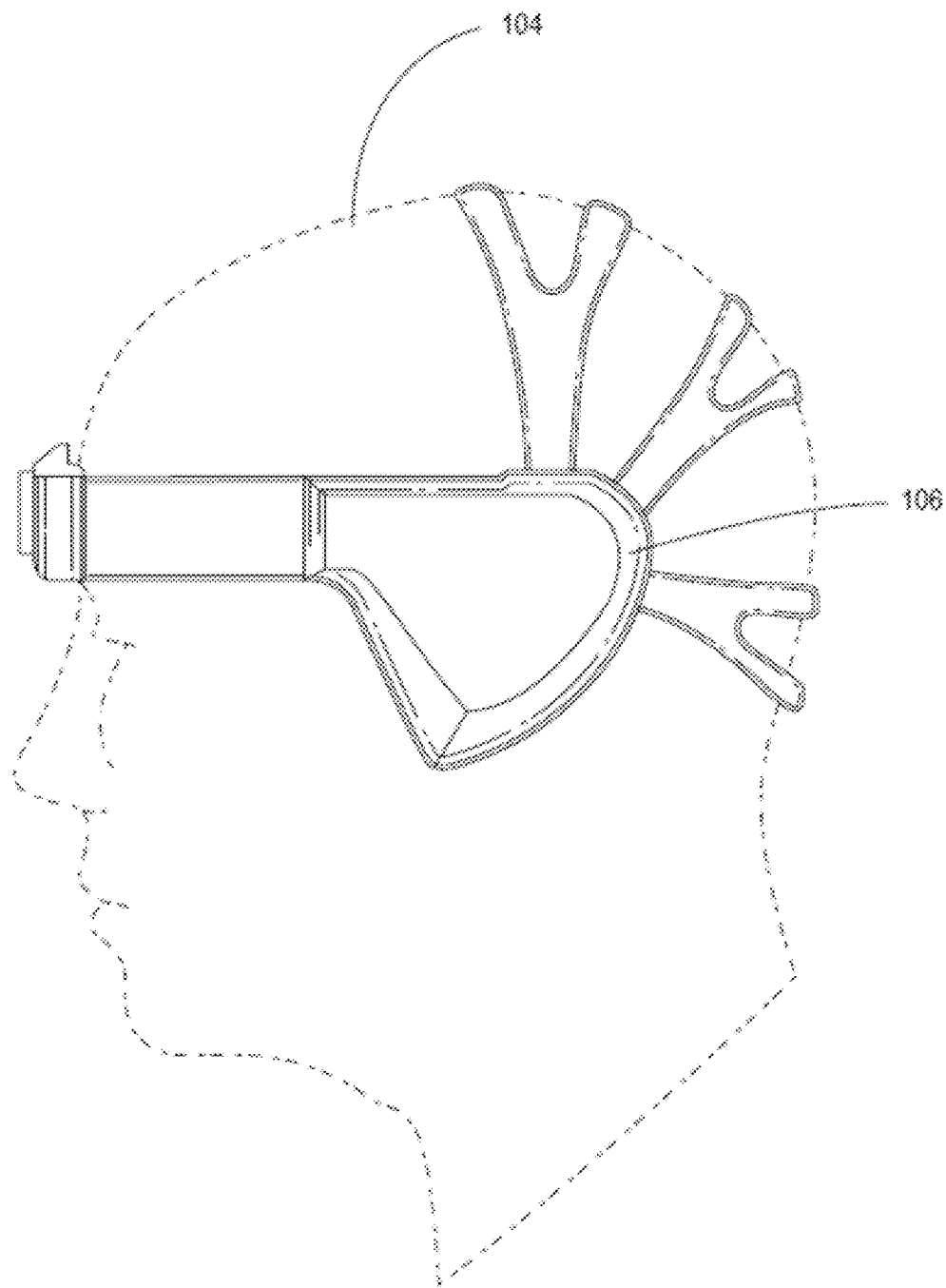
FIG. 2 illustrates a robotic headset for incorporating a TCD probe.

FIG. 2 illustrates a robotic headset 106 mounted on a human being's skull 104. To facilitate automated TCD scans without the use of a human operator manipulating a TCD probe, it would be advantageous to reduce the size of a TCD probe so that it would fit within a reasonably sized headset 106.

Figure 3:
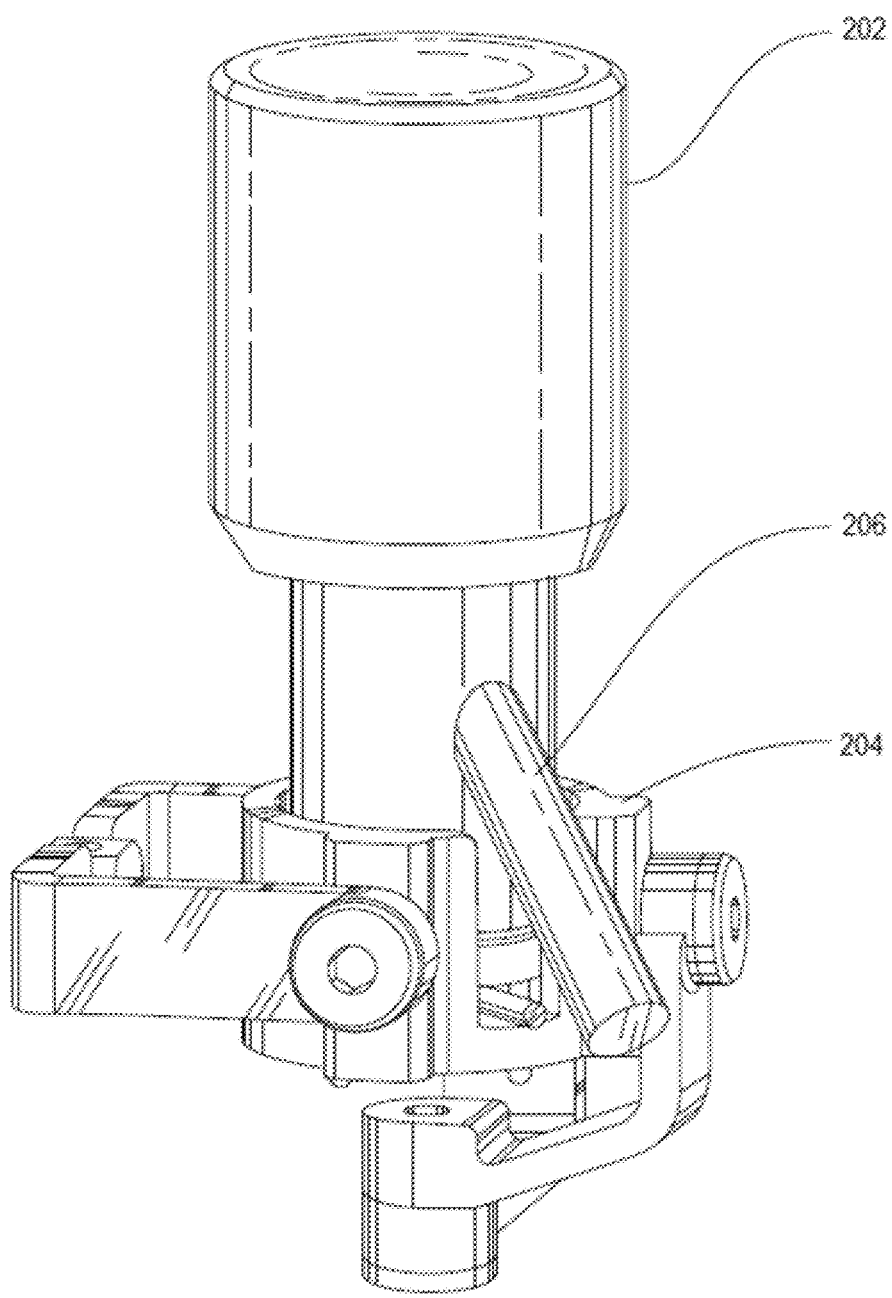
FIG. 3 illustrates a perspective view of an integrated TCD probe structure according to various embodiments.

FIG. 3 illustrates a perspective view of a TCD probe 202 mounted in a gimbal 204 for use in a robotic headset 106. While this specification frequently discusses TCD probes, in general, the techniques and devices discussed herein specifically described as using TCD can also be employed in various embodiments using probes for methods such as ultrasound, transcranial color-coded sonography (TCCS), phased arrays, as well as other known ultrasound energy modalities. Additionally, other techniques that use probes that emit or receive energy in the electromagnetic spectrum such as functional Near-Infrared Spectroscopy (fNIRS) or EEG can also be employed. In some embodiments, the gimbal 204 includes a pivoted support that allows for rotation of an object (e.g., the probe 202), about an axis (e.g., about a single axis). In some embodiments, the gimbal 204 is a probe hub. Further disclosure regarding the probe hub is described below. A data/power cable 206 allows for the flow of electricity to power the TCD probe 202 and the flow of data from the TCD probe 202. The gimbal 204 allows the TCD probe 202 to pan and tilt.

Figure 4:
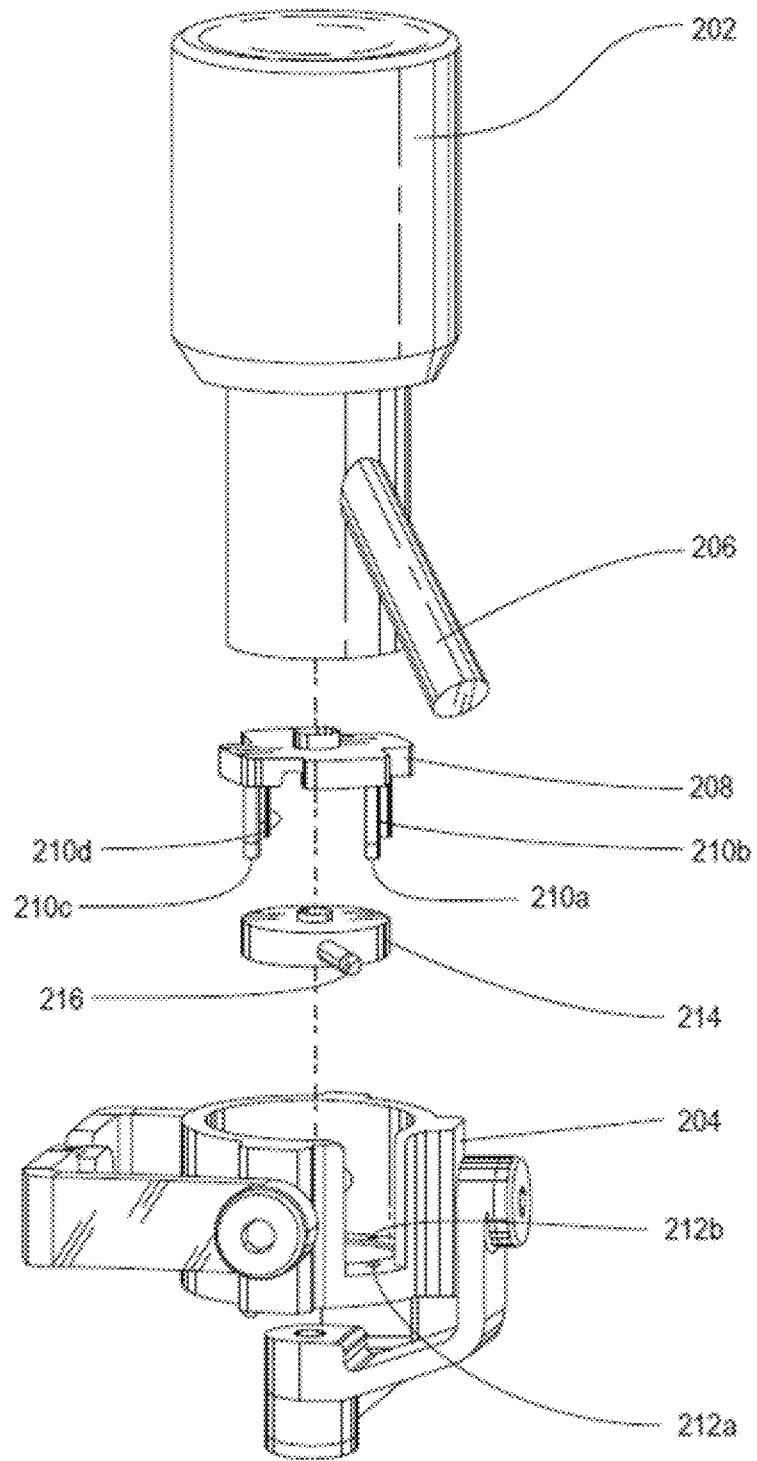
FIG. 4 is an exploded view of an integrated TCD probe structure according to various embodiments.

FIG. 4 illustrates an exploded view of the TCD probe 202 connection to the gimbal 204. To allow for connection of the TCD probe 202 to the gimbal 204, the TCD probe 202 is fastened, typically with glue, to a thrust plate 208. The thrust plate 208 has a plurality of legs 210a, 210b, 210c, 210d designed to mount in and align with corresponding receiving holes 212a, 212b (other holes 212c, 212d not shown). The thrust plate 208 is secured to the gimbal 204 by snap rings (not shown) on the bottom of the gimbal 204. Other methods of fastening known to those of skill in the art may also be employed, such as, but not limited to, interfacing (e.g., counter sunk features). A load cell 214 is fastened, typically with a form to fit counter sunk feature for initial alignment and with glue for stabilization, to the gimbal 204, and is designed to fit between the gimbal 204 and thrust plate 208. As is known in the art, a load cell 214 is a transducer that is used to translate physical phenomenon into an electrical signal whose magnitude is proportional to, in this case, the force being measured. Wires 216 extending from the load cell 214 provide electrical signals (e.g., data and power signals) emanating from the load cell 214 responsive to the force on the load cell 214. In operation, when the TCD probe 202 is pressed against a human being's skull 104, a force will also be imparted through the interfacing thrust plate 208 to the load cell 214, which will result in an electrical signal which can be measured.

Figure 5:
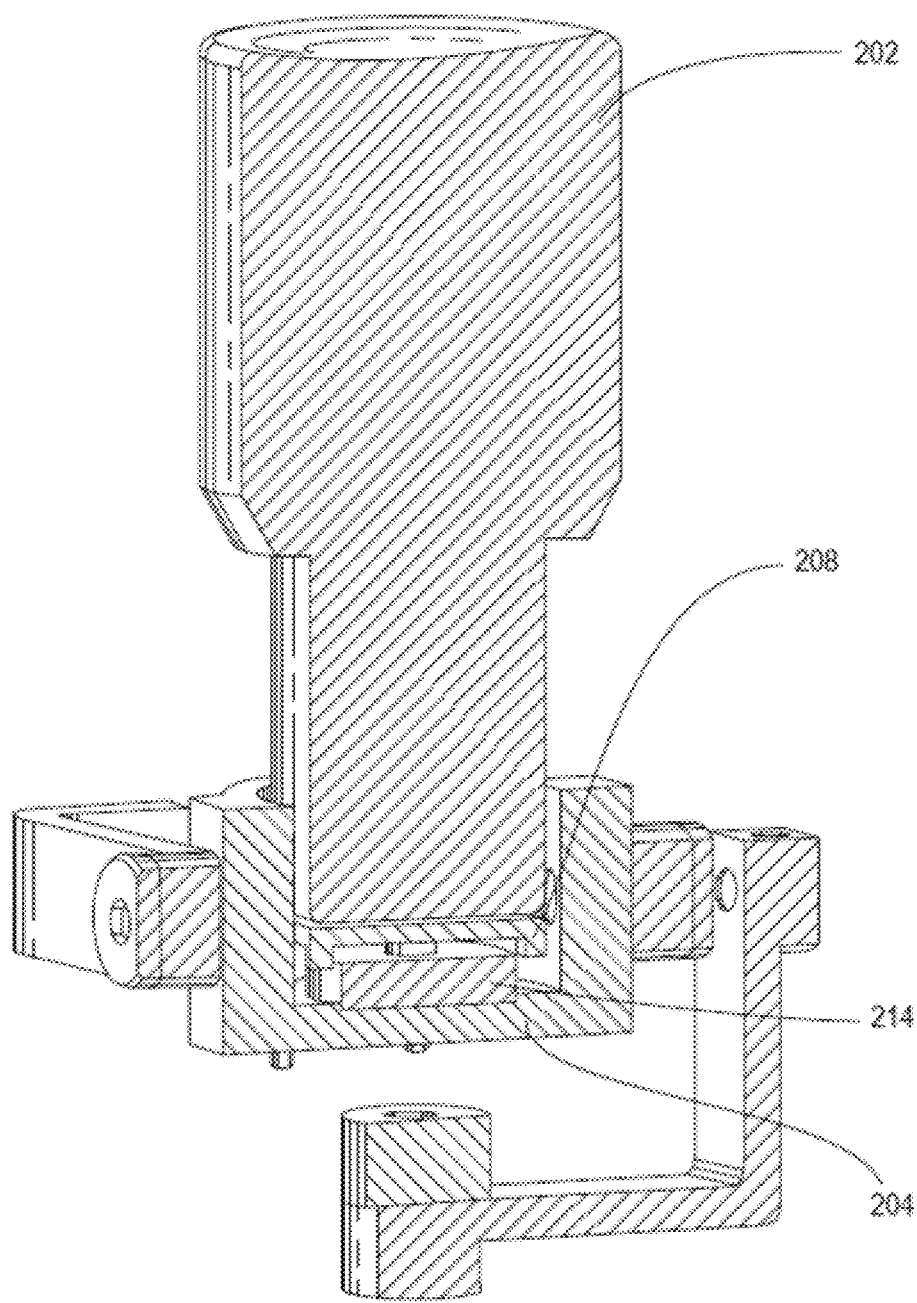
FIG. 5 illustrates a side cross-sectional view of an integrated TCD probe structure according to various embodiments.

FIG. 5 illustrates a perspective cross-sectional view of the of the TCD probe 202 connected to the thrust plate 208, which is in turn in contact with the load cell 214 connected to the gimbal 204.

Figure 6:
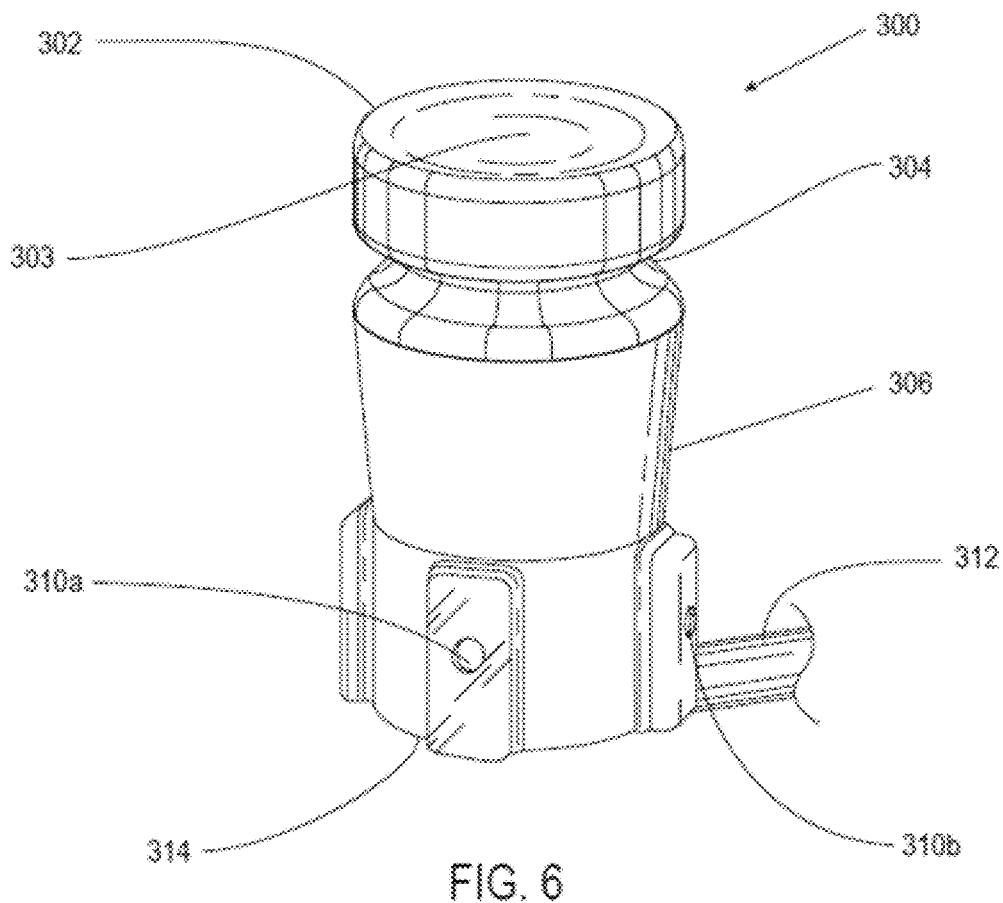
FIG. 6 illustrates a perspective view of an integrated gimbal probe structure according to various embodiments.
Figure 7:
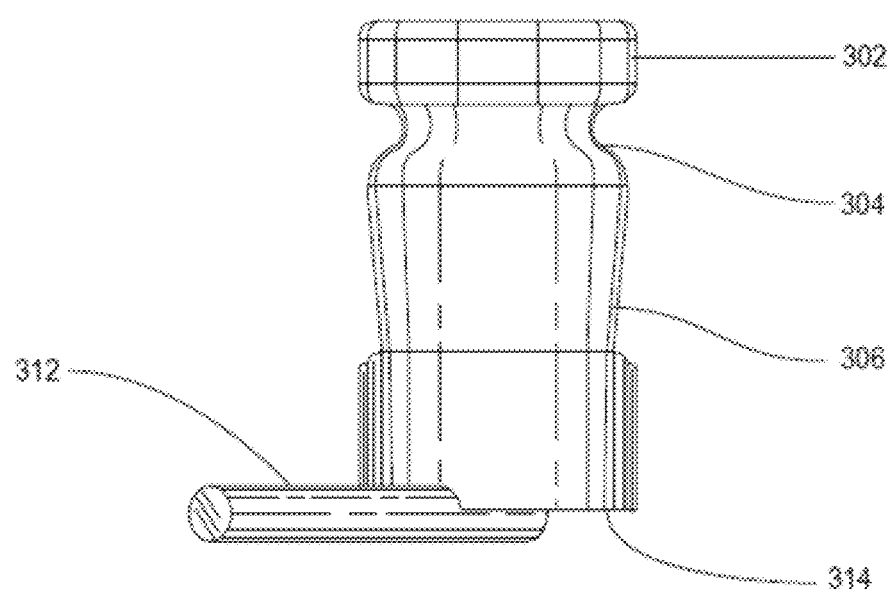
FIG. 7 illustrates a side view of an integrated gimbal probe structure according to various embodiments.
Figure 8:
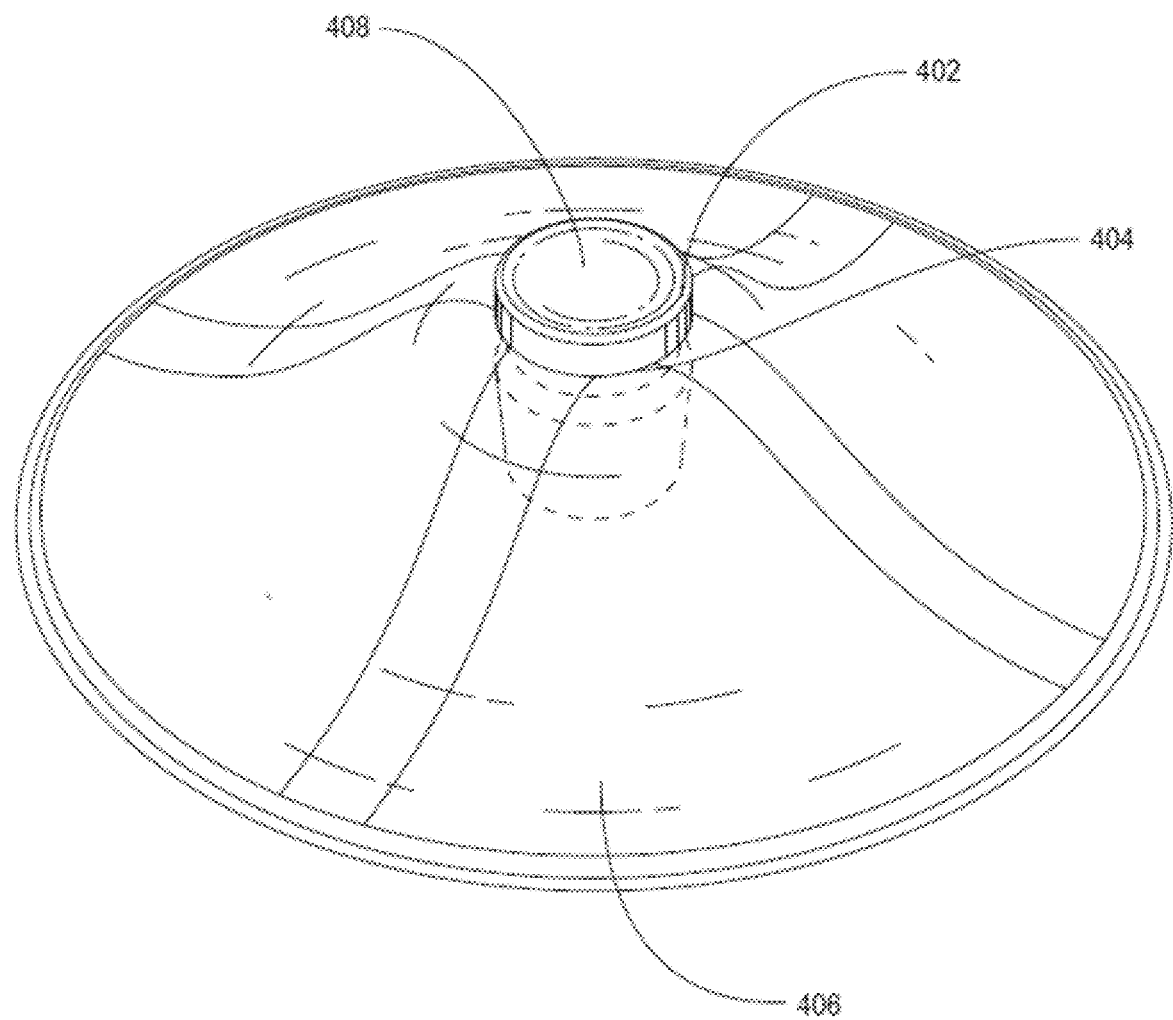
FIG. 8 illustrates a perspective view of a TCD probe adapted for use with an integrated gimbal probe structure with a cover according to various embodiments.

FIG. 6 illustrates a perspective view of a preferred embodiment of an integrated gimbal TCD probe 300 and FIG. 7 illustrates an elevation view of the integrated gimbal TCD probe 300. The integrated gimbal TCD probe 300 reduces the number of components compared to the embodiment of FIG. 4. The integrated gimbal TCD probe 300 has a TCD probe 302 capable of transmitting ultrasound waves into a human being's skull 104. The ultrasound waves are transmitted through the transducer face 303 which is pressed against the skin of a human being's skull 104. The TCD probe 302, rather than being cylinder shaped, has a tapered portion 304 adapted to receive a cover (as shown in FIG. 8). Beyond the tapered portion 304, the TCD probe 302 probe body 306 extends to a gimbal mount 314. The gimbal mount 314 has a plurality of tapped holes 310a, 310b, designed to mount with and allow for fastening of the gimbal mount 314 to a gimbal interface. A data/power cable 312 extends from the gimbal mount 314 of the integrated gimbal TCD probe 300 such that it has proper clearance from the gimbal.

FIG. 8 illustrates a TCD probe 402 having a shape similar to the integrated gimbal TCD probe 300 shown in FIG. 6. The TCD probe 402 has a tapered portion 404 adapted to receive a cover 406. The cover 406 mounts snugly to the tapered portion 404 to prevent a patient's skin from being pinched between the TCD probe 402 and any other mechanism of the robotic headset 106. Further, in operation, gel is typically placed on a transducer face 408 of the TCD probe 402 to provide improved conductivity between the skin of the patient and the transducer face 408. Employing a cover 406 snugly mounted with the tapered portion 404 will act to help prevent gel from moving past the tapered portion into the rest of the mechanism of the robotic headset 106. If gel were to move into the mechanism of the robotic headset 106, the gel may degrade operation of the robotic headset 106 or may require that the robotic headset 106 be cleaned from time to time to remove unwanted gel.

Figure 9:
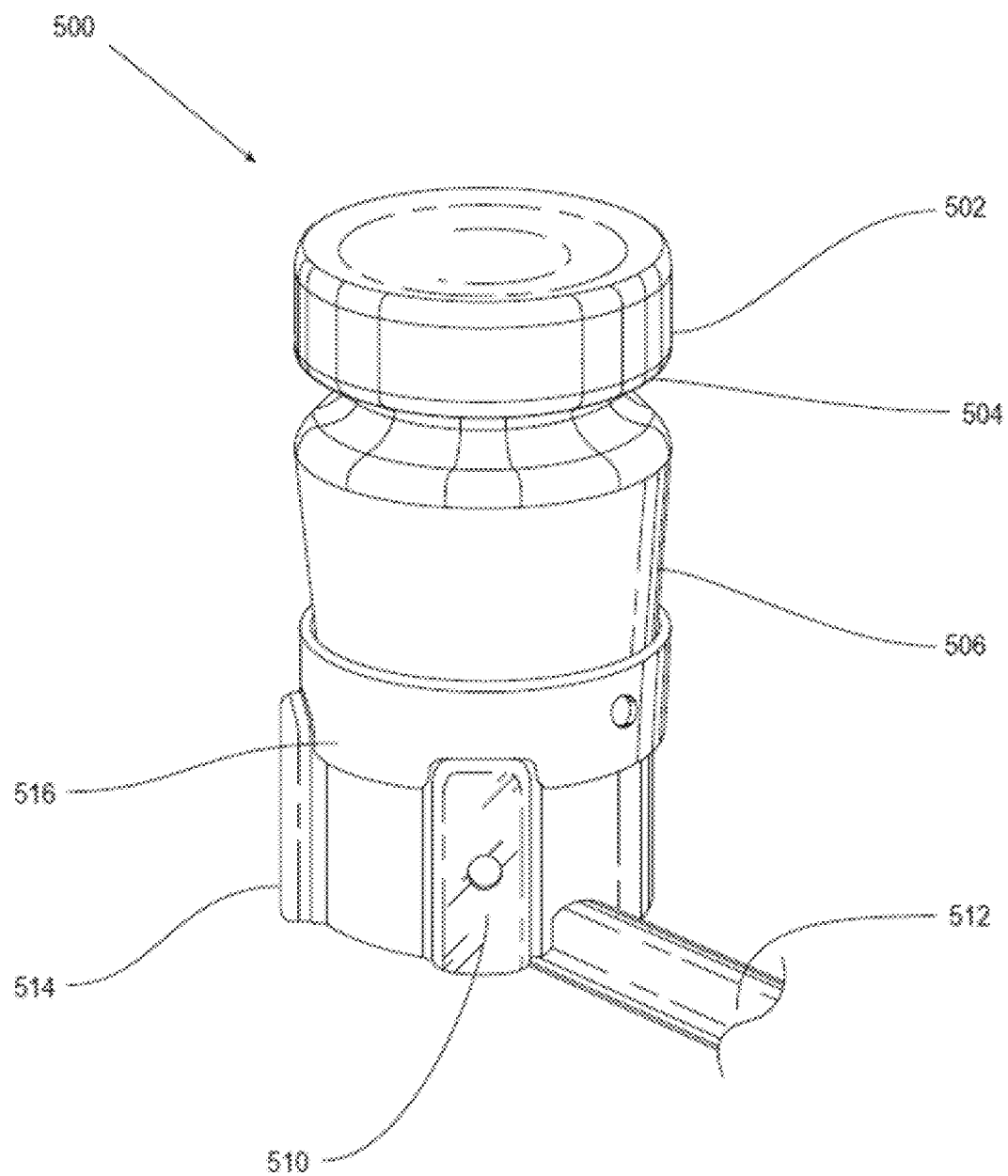
FIG. 9 illustrates a perspective view of an integrated force center probe according to various embodiments.

FIG. 9 illustrates a perspective view of an integrated force center probe 500. The integrated force center probe 500 includes a TCD probe 502 capable of transmitting ultrasound waves into a human being's skull 104. The TCD probe 502 has a tapered portion 504 adapted to receive a cover (as shown in FIG. 8). Below the tapered portion 504, the TCD probe 502 probe body 506 extends to a gimbal mount 514. Between the gimbal mount 514 and the probe body 506, an overmold piece 516 connects the gimbal mount 514 and the probe body 506. The gimbal mount 514 has a plurality of tapped holes 510 designed to mount with and allow for fastening of the gimbal mount 514 to a gimbal. A data/power cable 512 extends from the gimbal mount 514 of the integrated gimbal TCD probe 500 such that it has proper clearance from the gimbal.

Figure 10:
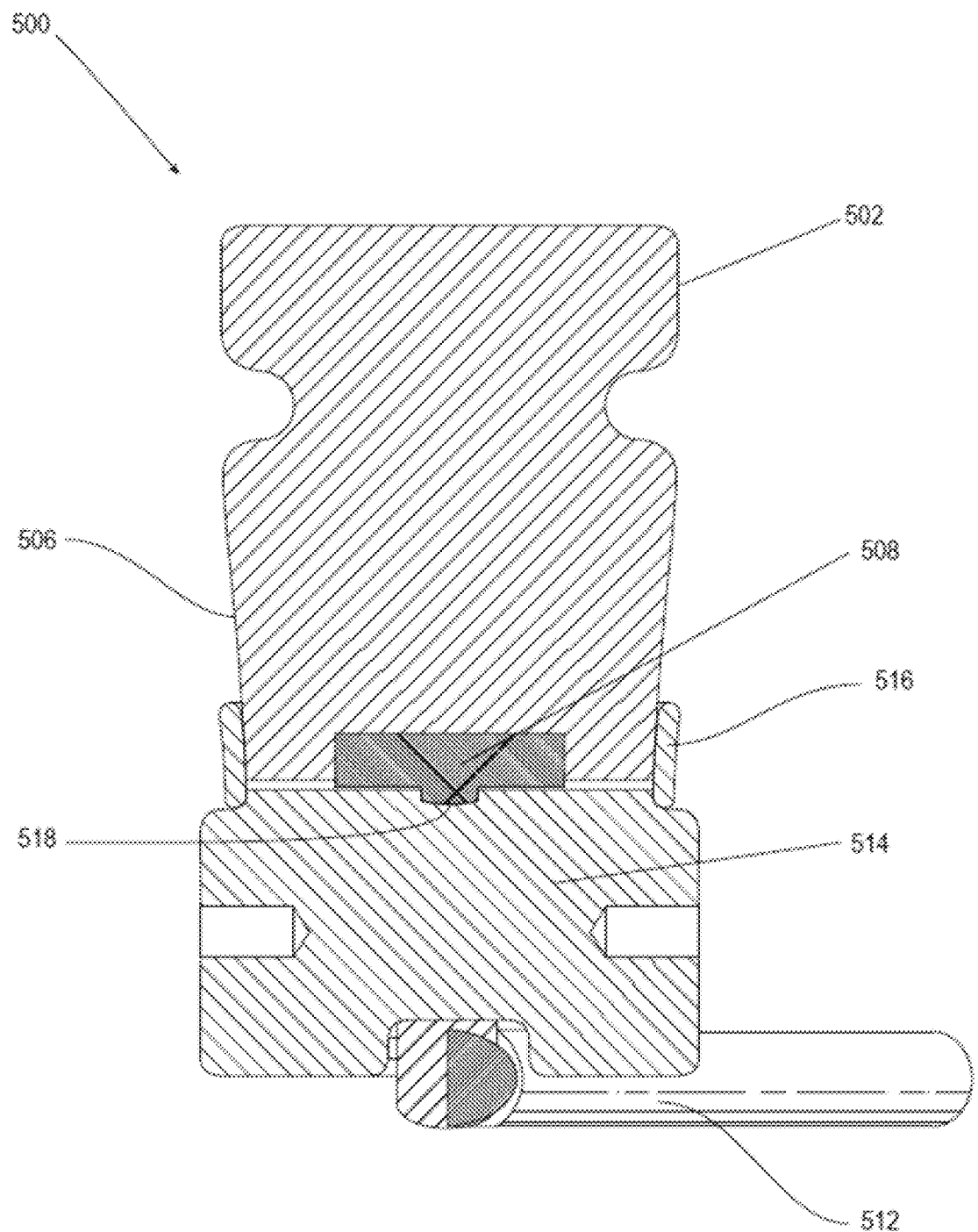
FIG. 10 illustrates a side cross-sectional view of a TCD probe adapted for use with a three piece integrated gimbal probe structure according to various embodiments.

FIG. 10 illustrates a cross-sectional side view of the integrated force center probe 500. A load cell 508 is molded into the bottom of TCD probe 502 having a probe body 506. The assembly of the load cell 508 and TCD probe 502 is then molded to gimbal mount 514 such that when the load cell 508 contacts the gimbal mount 514 a specific pre-defined preload is applied to a button 518 on the load cell 508. The gimbal mount 514 and probe body 506 are then molded together with an overmold piece 516. A data/power cable 512 extends from the gimbal mount 514 of the integrated force center probe 500 such that it has proper clearance from the gimbal.

Figure 11:
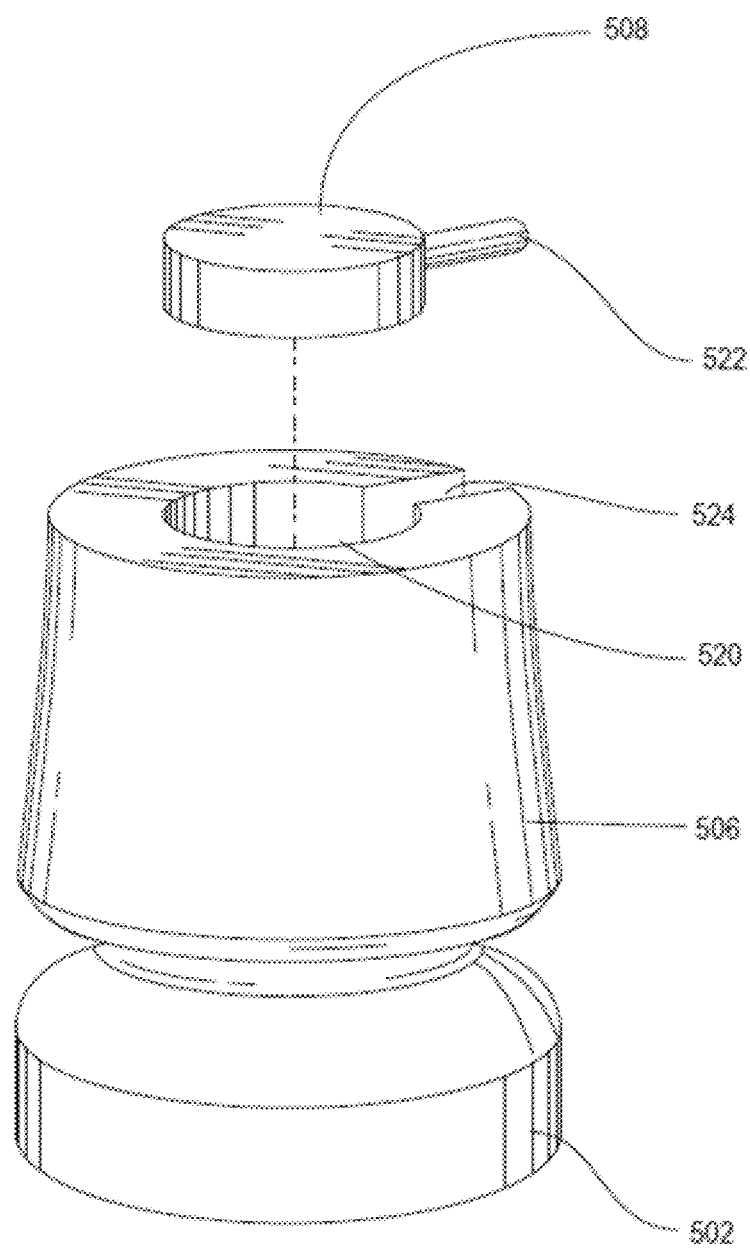
FIG. 11 illustrates a perspective exploded view of a TCD probe adapted for use with an integrated gimbal probe structure integrated with a cover according to various embodiments.

FIG. 11 illustrates a perspective view of an exploded portion of the integrated force center probe 500 oriented in a direction opposite that of FIG. 10. This view does not show the gimbal mount 514 or the data/power cable 512. Load cell 508 is mounted within a recess or countersink 520 of the probe body 506. Wires 522 extending from the load cell 508 provide electrical signals emanating from the load cell 508 responsive to the force on the load cell 508. The wires 522 exit the probe body 506 through a recess 524 in the probe body 506.

Figure 12A:
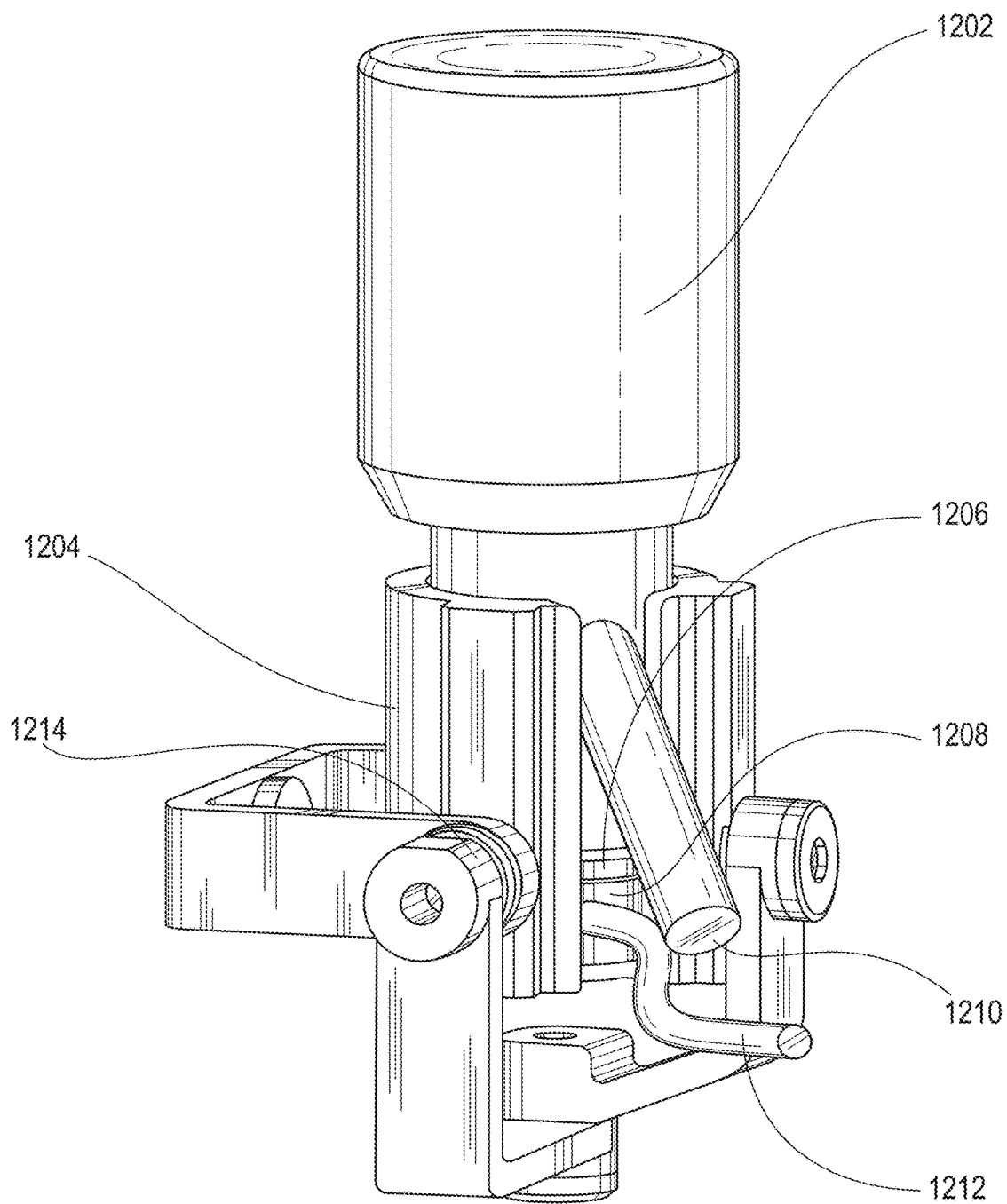
FIG. 12A illustrates a perspective view of an integrated probe structure according to various embodiments.
Figure 12B:
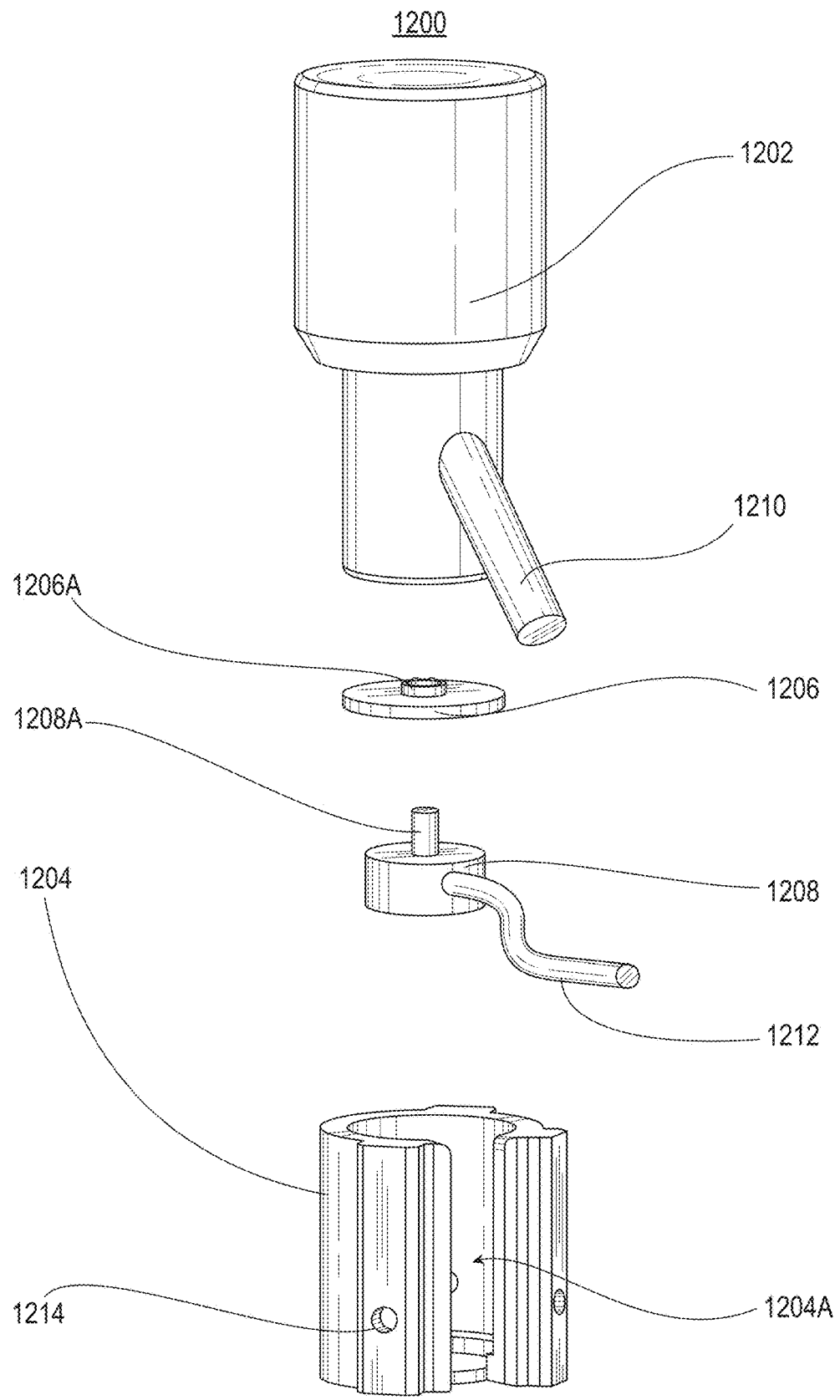
FIG. 12B illustrates an exploded view of the integrated probe structure shown in FIG. 12A according to various embodiments.
Figure 12C:
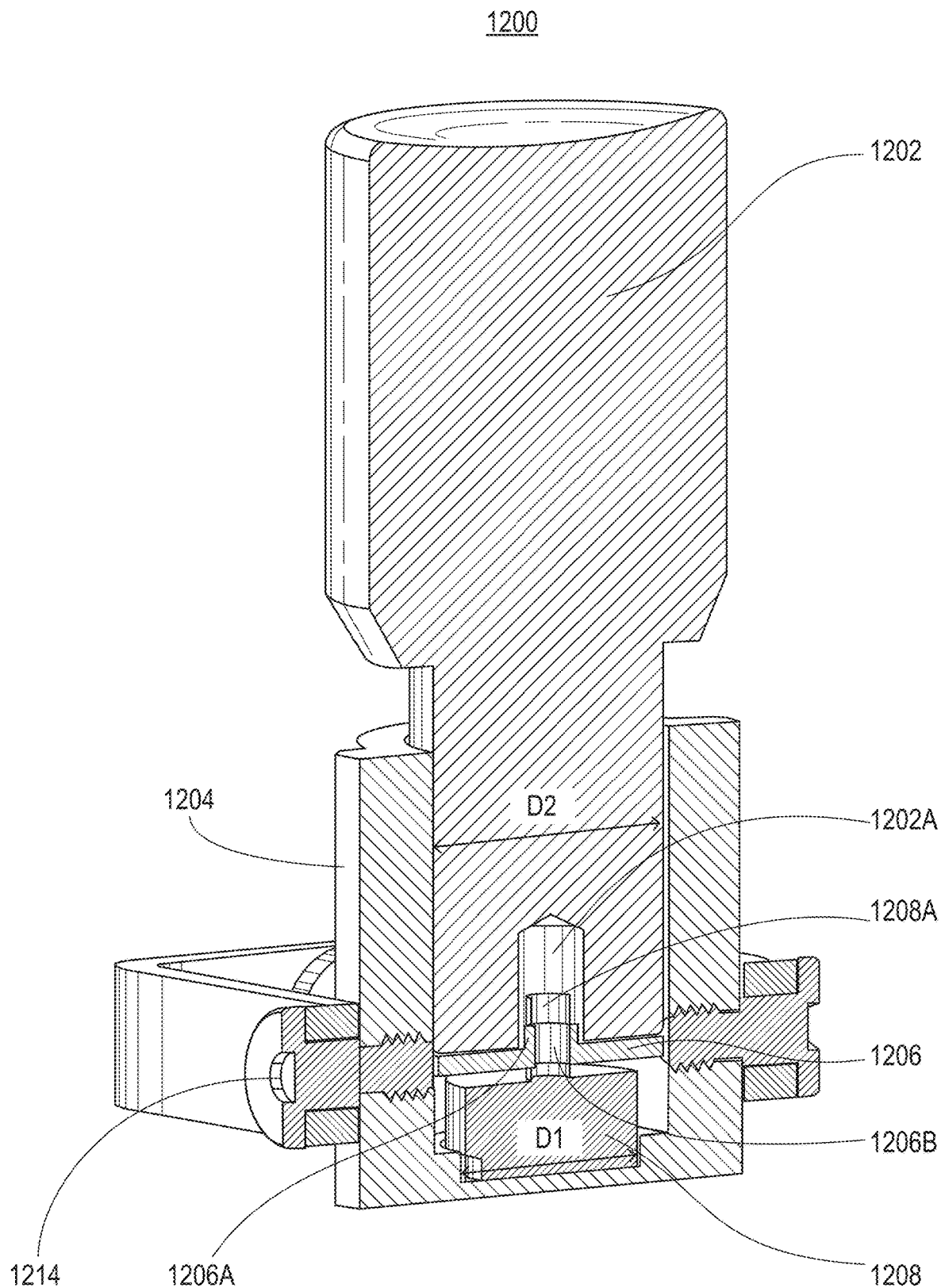
FIG. 12C illustrates a perspective cross-sectional view of the integrated probe structure shown in FIG. 12A according to various embodiments.

FIG. 12A illustrates a perspective view of an integrated probe structure 1200 according to various embodiments. FIG. 12B illustrates an exploded view of the integrated probe structure 1200 shown in FIG. 12A according to various embodiments. FIG. 12C illustrates a perspective cross-sectional view of the integrated probe structure 1200 shown in FIG. 12A according to various embodiments.

Referring to FIGS. 12A-12C, the probe structure 1200 includes a probe 1202, a probe hub or gimbal 1204, a probe seat 1206, and a load cell 1208. In some embodiments, the probe 1202 includes a first end (e.g., the end that is free and facing empty space) and a second end that is opposite to the first end. In some embodiments, the first end includes a concave surface that is configured to be adjacent to or contact a scanning surface. The concave surface is configured with a particular pitch to focus generated energy towards the scanning surface. In some embodiments, the probe structure is a Transcranial Doppler (TCD) apparatus such that the first end of the probe is configured to be adjacent to or contact and align along a human head (e.g., a side of the human head), and the first end of the probe 1202 is configured to provide ultrasound wave emissions from the first end and directed into the human head (e.g., towards the brain). In other embodiments, the probe 1202 is configured to emit other types of waves during operation, such as, but not limited to, infrared waves, x-rays, or the like.

In some embodiments, the second end of the probe 1202 is coupled to the probe seat 1206. The probe 1202 includes a hollow 1202A extending though the center of the probe 1202. In some embodiments, the hollow 1202A includes a threaded cavity-type interface. The hollow 1202A allows for alignment amongst the probe 1202, the probe seat 1206, and the load cell 1208. For example, the probe seat 1206 includes a circular ridge 1206A defining a through hole 1206B and the circular ridge 1206A extending upwards into the hollow 1202A of the probe 1202. The circular ridge 1206A includes a lip defining or housing a through hole, and the lip is fitted to extend upwards from the probe seat 1206. While the probe 1202 is coupled or attached to the probe seat 1206 at one side of the probe seat 1206, the load cell 1208 is coupled or attached to the opposite side of the probe seat 1206 such that the probe seat 1206 is interposed between the probe 1202 and the load cell 1208. Accordingly, in some embodiments, the probe seat 1206 is made from any suitable material for transferring the full or almost full force applied to the first end of the probe 1202 to the load cell 1208, such as, but not limited to, a non-metal material (e.g., polyurethane) and the like. In some embodiments, the probe structure 1200 does not include the probe seat 1206 such that the probe 1202 and the load cell 1208 contact each other.

In some embodiments, the probe seat 1206 is affixed to the probe 1202 through an adhesive layer. The adhesive layer may be any suitable material for securely coupling the probe seat 1206 and the probe 1202 together, such as, but not limited to, an epoxy. In other embodiments, the probe 1202 is secured in the probe seat 1206 by any other suitable connecting means, such as, but not limited to, welding, potting, one or more hooks and latches, one or more separate screws, press fittings, or the like.

In some embodiments, the load cell 1208 is coupled to the probe seat 1206. Accordingly, the probe seat 1206 may also function as a load cell register. In some embodiments, the load cell 1208 is configured to take measurements of pressure or force exerted on the probe 1202. In some embodiments, the load cell 1208 is assembled so as to exhibit a preload. For example, the load cell 1208 may be designed to exhibit and include a preload in a range from about 2 Newtons to about 3 Newtons. In some embodiments, because the load cell 1208 is aligned with and proximate the probe 1202 (e.g., coupled to the probe 1202 via the probe seat 1206), a force exerted against the concave surface of the first end of the probe 1202 (e.g., caused by the concave surface being pressed against a human head), is registered and measured at the load cell 1208.

In some embodiments, the load cell 1208 is a transducer that is used to create an electrical signal whose magnitude is proportional to the force being measured. In some embodiments, a wire 1212 extending from the load cell 1208 provides electrical signals generated from the load cell 1208, responsive to the force on the load cell 1208 caused by the probe 1202. During operation, in some embodiments, when the probe 1202 is pressed against a human skull, a force will also be imparted through the probe seat 1206 to the load cell 1208, which can be measured and transmitted by the load cell 1208.

Accordingly, in some embodiments, the probe structure 1200 utilizes the measurements of the load cell 1208 to adjust the pressure exerted by the probe 1202 (e.g., by a robotic apparatus attached to the probe structure 1200). For example, in some embodiments, the probe structure 1200 decreases the force exerted against a human head by the probe 1202 when the pressure measured by the load cell 1208 is determined to be relatively high (e.g., the pressure measurement exceeds a predetermined threshold). In some embodiments, the predetermined threshold is user-defined and can be adjusted as desired.

In some embodiments, the load cell 1208 includes a cylindrical protrusion 1208A extending upwards from the load cell 1208. The protrusion 1208 passes through the through hole 1206B of the probe seat 1206 and extends into the hollow 1202A (or the threaded cavity-type interface of the hollow 1202A) of the probe 1202. Accordingly, the probe 1202, the probe seat 1206, and the load cell 1208 are capable of remaining aligned such that a maximum amount of forced is transferred from the probe 1202 to the load cell 1208. In some embodiments, the load cell 1208 is affixed to a bottom inner surface of the probe hub (or gimbal) 1204 through an adhesive layer. The adhesive layer may be any suitable material for securely coupling the load cell 1208 and the probe hub 1204 together, such as, but not limited to, an epoxy, potting, and the like.

In some embodiments, the probe hub 1204 provides a plurality of single axis pivoted supports and interfaces with links and motors to provide a pan and tilt about respective Y and X axes. In some embodiments, the probe hub 1204 is a gimbal as described above. In some embodiments, the probe hub 1204 has a fitted cavity for receiving and housing a portion of the probe 1202, the probe seat 1206, and the load cell 1208 to provide further security and alignment of the probe structure 1200. The cavity of the probe hub (or gimbal) 1204 includes a counter sunk first inner diameter D1 that corresponds to a location of the load cell 1208 when the load cell 1208 is housed within the probe hub 1204. The first diameter D1 is substantially equal to (e.g., slightly larger than) an outer diameter of the load cell 1208 such that the load cell 1208 does not shift radially while housed in the probe hub (or gimbal) 1204. Accordingly, the load cell 1208 remains axially aligned with the probe seat 1206 and a shaft end of the probe 1202.

Similarly, the cavity of the probe hub 1204 includes a second inner diameter D2 that corresponds to a location of the probe 1202 and the probe seat 1206 when the probe 1202 and the probe seat 1206 are housed within the probe hub 1204. The second inner diameter D2 is substantially equal to (e.g., slightly larger than) an outer diameter of the shaft end of the probe 1202 and the probe seat 1206 such that the probe 1202 and the probe seat 1206 do not shift radially while housed in the probe hub 1204. Accordingly, the probe 1202 and the probe seat 1206 remains axially aligned with the load cell 1208. In some embodiments, the second inner diameter D2 is greater than the first inner diameter D1.

In some embodiments, the probe hub (or gimbal) 1204 has a length long enough to encompass and house the load cell 1208 (e.g., entirely), the probe seat 1206 (e.g., entirely), and a portion (e.g., a substantial portion) of the probe 1202. In some embodiments, the probe hub 1204 is long enough to house approximately 50% of the length of the body of the probe 1202. In other embodiments, the probe hub 1204 is long enough to house more than 50% of the length of the body of the probe 1202 (e.g., about 55%, 60%, 65%, or more). In other embodiments, the probe hub 1204 houses less than 50% of the length of the body of the probe 1202 (e.g., about 45%, 40%, 35%, or less). In particular embodiments, the probe hub 1204 house about 33% of the length of the body of the probe 1202.

In some embodiments, the probe hub 1204 includes a lengthwise slot 1204A. The slot 1204A may extend along the full length of the body of the probe hub 1204. In other embodiments, the slot 1204A extends along less than the full length of the body of the probe hub 1204. The slot 1204A is configured to receive and retain wires and cables originating from the components housed within the probe hub 1204. For example, the slot 1204A receives and retains the wire 1212 originating from the load cell 1208 and a cable 1210 originating from the probe 1202. Accordingly, the wire 1212 and the cable 1210 can be aligned and secured (e.g., during assembly and outside of the probe hub or gimbal 1204) so that they do not become an obstacle during assembly or operation of the probe structure 1200. In some embodiments, the wire 1212 remains static in the slot 1204A, while the cable 1210 is configured to move within the slot 1204A (e.g., flex or otherwise move along the length of the slot 1204A). In some embodiments, the probe hub 1204 further includes a gimbal interface 1214 for attaching to gimbal linkages that can control the probe structure 1200.

Figure 13A:
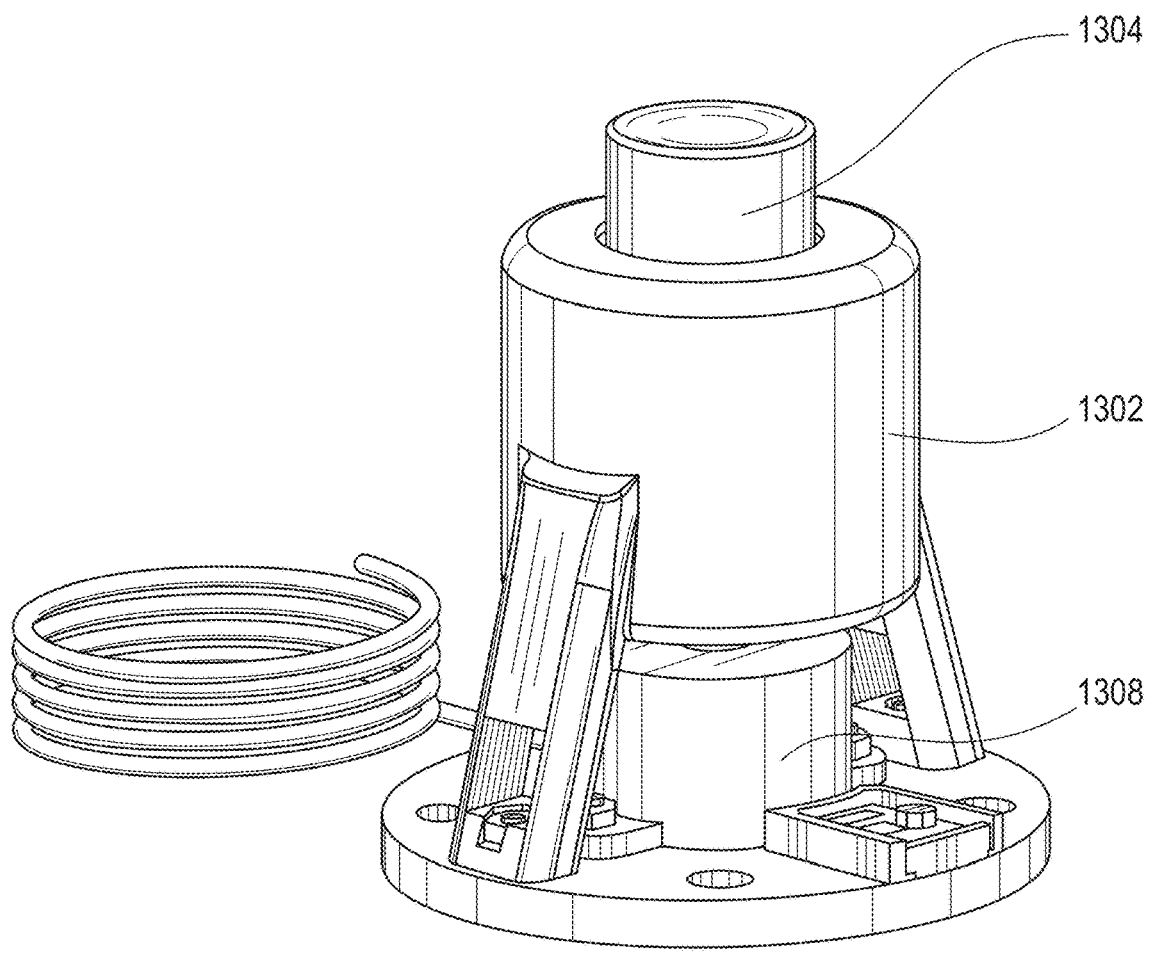
FIG. 13A illustrates a perspective view of an integrated probe structure according to various embodiments.
Figure 13B:
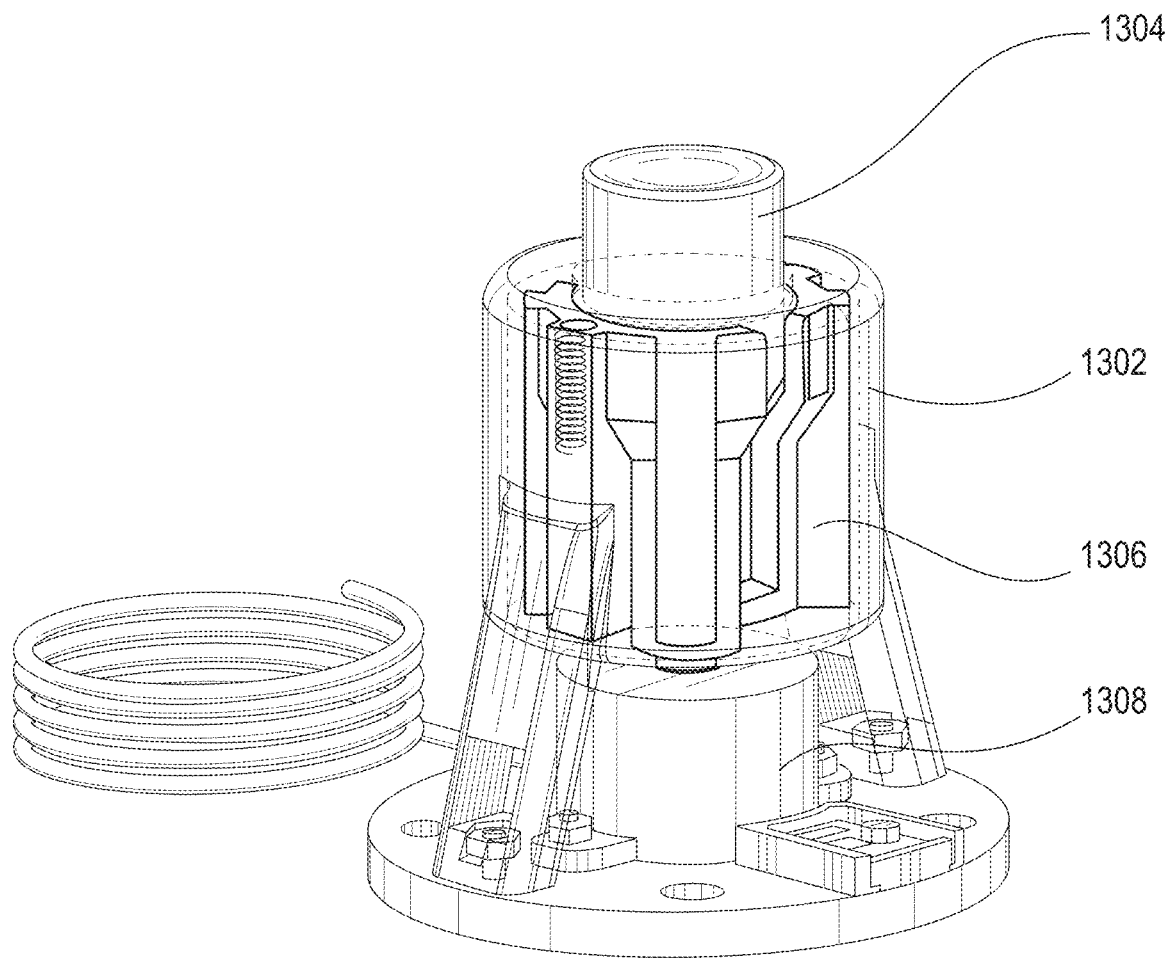
FIG. 13B illustrates a transparent perspective view of the integrated probe structure shown in FIG. 13A according to various embodiments.
Figure 13C:
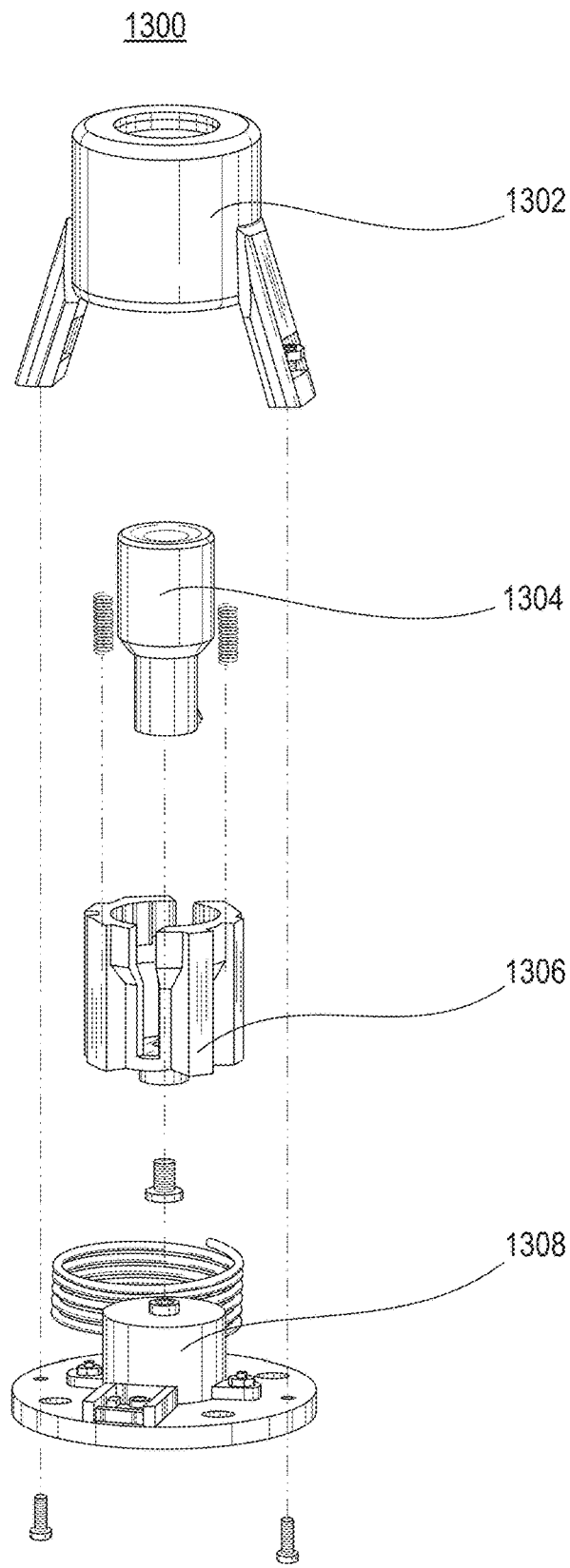
FIG. 13C illustrates an exploded view of the integrated probe structure shown in FIG. 13A according to various embodiments.

FIG. 13A illustrates a perspective view of an integrated probe structure 1300 according to various embodiments. FIG. 13B illustrates a transparent probe housing in a perspective view of the integrated probe structure 1300 shown in FIG. 13A according to various embodiments. FIG. 13C illustrates an exploded view of the integrated probe structure 1300 shown in FIG. 13A according to various embodiments.

The probe structure 1300 includes a probe housing 1302, a probe 1304, an interconnection structure 1306, and a load cell 1308. In some embodiments, the probe structure 1300 includes an end effector, for example, used in conjunction with a robot arm (e.g., a 6-axis robot arm). The probe housing 1302 covers and houses the probe 1304, the interconnection structure 1306, and the load cell 1308. The probe 1304 extends through a top opening of the probe housing 1302. The interconnection structure 1306 provides the framework of the probe structure 1300 for securing the components together. The load cell 1308 is located adjacent to the probe 1304 (e.g., directly underneath the probe 1304). The probe structure 1300 can be used in connection with a robotic arm (e.g., a robotic arm including multiple degrees of freedom, such as, but not limited to, six degrees of freedom).

Although the present disclosure illustrates and describes an integrated probe system including a load cell for detecting force exerted against a probe in a single axis (e.g., along an axis that is perpendicular to the upper surface of the probe facing a scanning surface), in some embodiments, the load cell and the integrated probe system may be configured to detect forces in a plurality of axes. For example, the integrated probe system may be configured to detect force exerted against the probe along two axes, three axes, four axes, five axes, or six axes. In some embodiments, the probe is continuously adjusted to maintain a normal position along a scanning surface using a load cell that detects force along a plurality of axes (e.g., along six different axes).

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same or equal if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

The above used terms, including "attached," "connected," "secured," and the like are used interchangeably. In addition, while certain embodiments have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

What is claimed is:

1. An ultrasound device for use on a subject, the device comprising:
   a probe that emits acoustic energy and that defines a hollow;
   a load cell underneath and aligned with the probe, the load cell comprising a protrusion, wherein the load cell determines a force reading indicating an amount of force exerted against the subject by the probe, and wherein the hollow of the probe receives the protrusion of the load cell for securing the load cell and the probe together;
   a probe hub, wherein the probe hub defines a cavity for receiving the probe and the load cell; and
   a gimbal structure connected to the probe hub, the gimbal structure configured to allow the probe hub to pan and tilt about a first plurality of axes.

2. The device of claim 1, wherein the probe further comprises a probe seat interposed between the probe and the load cell.

3. The device of claim 1, wherein the probe comprises a tapered portion.

4. The device of claim 3, wherein the tapered portion is configured to receive a cover and attach the cover to the probe.

5. The device of claim 4, wherein the cover is made of a material impermeable to gel.

6. The device of claim 1, wherein the probe further comprises an adhesive layer between the load cell and a bottom of the cavity of the probe hub.

7. The device of claim 1, wherein the probe further comprises a probe seat interposed between the probe and the load cell and an adhesive layer between the probe and the probe seat.

8. The device of claim 7, wherein the adhesive layer comprises epoxy.

9. The device of claim 1, wherein the probe further comprises a probe seat interposed between the probe and the load cell, wherein the probe seat has a through hole such that the protrusion of the load cell threads through the through hole and the hollow of the probe.

10. The device of claim 1, wherein the probe hub is configured to house the load cell and a portion of the probe.

11. The device of claim 10, wherein the cavity of the probe hub comprises an inner diameter that is substantially equal to an outer diameter of the portion of the probe.

12. The device of claim 10, wherein the cavity of the probe hub comprises a first inner diameter corresponding to a location of the portion of the probe housed within the cavity and a second inner diameter corresponding to a location of the load cell housed within the cavity, the first inner diameter being different from the second inner diameter.

13. The device of claim 12, wherein the first inner diameter is greater than the second inner diameter.

14. The device of claim 12, wherein the first inner diameter is substantially equal to an outer diameter of the portion of the probe and the second inner diameter is substantially equal to an outer diameter of the load cell.

15. The device of claim 12, wherein the probe further comprises a probe seat interposed between the probe and the load cell, wherein the first inner diameter further corresponds to a location of the probe seat housed within the cavity.

16. The device of claim 1, wherein the load cell is configured to detect forces exerted against the probe along a second plurality of axes.

17. The device of claim 1, further comprising an automated robotic structure configured to decrease the amount of force exerted against the subject in response to the force reading being above a first threshold.

18. The device of claim 17, wherein the automated robotic structure is configured to increase the amount of force exerted against the subject in response to the force reading being below a second threshold.

19. The device of claim 18, wherein the automated robotic structure is contained within the probe hub.

20. A method of manufacturing an ultrasound device for use on a subject, the method comprising:

provising a probe hub, wherein the probe hub defines a cavity;

providing a probe that emits acoustic energy and that defines a hollow into the cavity;

securing a load cell that comprises a protrusion to an underside of the probe, wherein the load cell determines a force reading indicating an amount of force exerted against the subject by the probe, wherein the hollow of the probe receives the protrusion of the load cell for securing the load cell and the probe together;

inserting the probe secured to the load cell into the cavity of the probe hub;

securing the load cell to the probe hub; and attaching a gimbal structure to the probe hub.

* * * * *